United States Patent
Bouchon et al.

(10) Patent No.: US 7,615,557 B2
(45) Date of Patent: Nov. 10, 2009

(54) TETRAHYDRO-NAPHTHALENE AND UREA DERIVATIVES

(75) Inventors: Axel Bouchon, Cologne (DE); Nicole Diedrichs, Wuppertal (DE); Achim Hermann, Dusseldorf (DE); Klemens Lustig, Wuppertal (DE); Heinrich Meier, Wuppertal (DE); Josef Pernerstorfer, Hilden (DE); Elke Reissmuller, Wuppertal (DE); Jean De Vry, Stolberg (DE); Muneto Mogi, Nara (JP); Klaus Urbahns, Hyogo (JP); Takeshi Yura, Nara (JP); Hiroshi Fujishima, Nara (JP); Masaomi Tajimi, Kyoto (JP); Noriyuki Yamamoto, Nara (JP); Yasuhiro Tsukimi, Amagasaki (JP); Hiroaki Yuasa, Soraku-gun (JP); Jang Gupta, Higashinada-ku (JP); Fumihiko Hayashi, Soraku-gun (JP)

(73) Assignee: Xention Limited, Cambridgeshire (GB)

( * ) Notice: Subject to any disclaimer, the term of this patent is extended or adjusted under 35 U.S.C. 154(b) by 152 days.

(21) Appl. No.: 10/574,122

(22) PCT Filed: Sep. 22, 2004

(86) PCT No.: PCT/EP2004/010606

§ 371 (c)(1),
(2), (4) Date: Nov. 22, 2006

(87) PCT Pub. No.: WO2005/040119

PCT Pub. Date: May 6, 2005

(65) Prior Publication Data
US 2007/0167458 A1      Jul. 19, 2007

(30) Foreign Application Priority Data

Oct. 1, 2003  (EP) ................................. 03022235
Nov. 8, 2003  (EP) ................................. 03025570

(51) Int. Cl.
*A01N 43/40* (2006.01)
*A61K 31/445* (2006.01)
*A61K 31/4965* (2006.01)
*C07D 295/00* (2006.01)
*C07D 241/04* (2006.01)

(52) U.S. Cl. .................. 514/255.01; 514/319; 544/390
(58) Field of Classification Search ............ 514/255.01, 514/319; 544/390; 546/184, 185
See application file for complete search history.

(56) References Cited

FOREIGN PATENT DOCUMENTS

| WO | WO 02/08221 A2 | 1/2002 |
|----|----|----|
| WO | WO 03/014064 A1 | 2/2003 |
| WO | WO 03/068749 | * 2/2003 |
| WO | WO 03/022809 A2 | 3/2003 |
| WO | WO 03/068749 A1 | 8/2003 |
| WO | WO 2004/052845 A1 | 6/2004 |

OTHER PUBLICATIONS

Walker, et al., The VR1 Antagonist Capsazepine Reverses Mechanical Hyperalgesia in Models of Inflammatory and Neuropathic Pain, J. of Pharm. and Exper. Ther., vol. 304, No. 1, pp. 56-62 (2003).*
Patent Abstract of Japan, vol. 2003, No. 11, Nov. 5, 2003 & JP 2003 192673 A (Bayer AG).
Office Action dated Apr. 19, 2007 in connection with U.S. Appl. No. 10/537,217.
Office Action dated Nov. 30, 2007 in connection with U.S. Appl. No. 10/537,217.
Office Action dated Jul. 2, 2008 in connection with U.S. Appl. No. 10/537,217.
Office Action dated Jan. 13, 2009 in connection with U.S. Appl. No. 10/513,848.

* cited by examiner

*Primary Examiner*—James O Wilson
*Assistant Examiner*—Erich A Leeser
(74) *Attorney, Agent, or Firm*—Baker Botts LLP

(57) ABSTRACT

This invention relates to a hydroxy-tetrahydro-naphthalene or an urea derivative formula (I) and salts thereof which are useful as active ingredients of pharmaceutical preparations, wherein A represents formula (II) or (III) wherein # represents the connection position to the molecule and $Q_{1a}$, $Q_{2a}$, $Q_{3a}$ and $Q_{4a}$ are defined, and E represents formula (IV) or (V) wherein # represents the connection position to the molecule and $Q_{1b}$, $Q_{2b}$, $Q_{3b}$, $Q_{4b}$, $Q_{5b}$, $R^{1b}$, na, ma, $X_a$ and $R_a$ are defined.

26 Claims, No Drawings

TETRAHYDRO-NAPHTHALENE AND UREA DERIVATIVES

DETAILED DESCRIPTION OF INVENTION

1. Technical Field

The present invention relates to a hydroxy-tetrahydronaphthalene or an urea derivative which is useful as an active ingredient of pharmaceutical preparations. The hydroxy-tetrahydro-naphthalene and urea derivatives of the present invention have vanilloid receptor (VR1) antagonistic activity, and can be used for the prophylaxis and treatment of diseases associated with VR1 activity, in particular for the treatment of urological diseases or disorders, such as detrusor overactivity (overactive bladder), urinary incontinence, neurogenic detrusor overactivity (detrusor hyperflexia), idiopathic detrusor overactivity (detrusor instability), benign prostatic hyperplasia, and lower urinary tract symptoms; chronic pain, neuropathic pain, postoperative pain, rheumatoid arthritic pain, neuralgia, neuropathies, algesia, nerve injury, ischaemia, neurodegeneration, stroke, and inflammatory disorders such as asthma and chronic obstructive pulmonary (or airways) disease (COPD).

2. Background Art

Vanilloid compounds are characterized by the presence of vanillyl group or a functionally equivalent group. Examples of several vanilloid compounds or vanilloid receptor modulators are vanillin (4-hydroxy-3-methoxy-benzaldehyde), guaiacol (2-methoxy-phenol), zingerone (4-/4-hydroxy-3-methoxyphenyl/-2-butanon), eugenol(2-methoxy4-/2-propenyl/phenol), and capsaicin (8-methy-N-vanillyl-6-noneneamide).

Among others, capsaicin, the main pungent ingredient in "hot" chili peppers, is a specific neurotoxin that desensitizes C-fiber afferent neurons. Capsaicin interacts with vanilloid receptors (VR1), which are predominantly expressed in cell bodies of dorsal root ganglia (DRG) or nerve endings of afferent sensory fibers including C-fiber nerve endings [Tominaga M, Caterina M J, Malmberg A B, Rosen T A, Gilbert H, Skinner K, Raumann B E, Basbaum A I, Julius D: The cloned capsaicin receptor integrates multiple pain-producing stimuli. Neuron. 21: 531-543, 1998]. The VR1 receptor was recently cloned [Caterina M J, Schumacher M A, Tominaga M, Rosen T A, Levine J D, Julius D: Nature 389: 816-824, (1997)] and identified as a nonselective cation channel with six tranrmembrane domains that is structurally related to the TRP (transient receptor potential) channel family. Binding of capsaicin to VR1 allows sodium, calcium and possibly potassium ions to flow down their concentration gradients, causing initial depolarization and release of neurotransmitters from the nerve terminals. VR1 can therefore be viewed as a molecular integrator of chemical and physical stimuli that elicit neuronal signals in pathological conditions or diseases.

There is abundant direct or indirect evidence that shows the relation between VR1 activity and diseases such as pain, ischaemia, and inflammatory disorders (e.g., WO 99/00115 and 00/50387). Further, it has been demonstrated that VR1 transduces reflex signals that are involved in the overactive bladder of patients who have damaged or abnormal spinal reflex pathways [De Groat W C: A neurologic basis for the overactive bladder. Urology 50 (6A Suppl): 36-52, 1997]. Desensitisation of the afferent nerves by depleting neurotransmitters using VR1 agonists such as capsaicin has been shown to give promising results in the treatment of bladder dysfunction associated with spinal cord injury and multiple sclerosis [(Maggi C A: Therapeutic potential of capsaicin-like molecules—Studies in animals and humans. Life Sciences 51: 1777-1781, 1992) and (DeRidder D; Chandiramani V; Dasgupta P; VanPoppel H; Baert L; Fowler C J: Intravesical capsaicin as a treatment for refractory detrusor hyperreflexia: A dual center study with long-term follow-up. J. Urol. 158: 2087-2092, 1997)].

It is anticipated that antagonism of the VR1 receptor would lead to the blockage of neurotransmitter release, resulting in prophylaxis and treatment of the conditions and diseases associated with VR1 activity.

It is therefore expected that antagonists of the VR1 receptor can be used for prophylaxis and treatment of the conditions and diseases including chronic pain, neuropathic pain, postoperative pain, rheumatoid arthritic pain, neuralgia, neuropathies, algesia, nerve injury, ischaemia, neurodegeneration, stroke, inflammatory disorders, urinary incontinence (UI) such as urge urinary incontinence (UUI), and/or overactive bladder.

UI is the involuntary loss of urine. UUI is one of the most common types of UI together with stress urinary incontinence (SUI) which is usually caused by a defect in the urethral closure mechanism. UUI is often associated with neurological disorders or diseases causing neuronal damages such as dementia, Parkinson's disease, multiple sclerosis, stroke and diabetes, although it also occurs in individuals with no such disorders. One of the usual causes of UUI is overactive bladder (OAB) which is a medical condition referring to the symptoms of frequency and urgency derived from abnormal contractions and instability of the detrusor muscle.

There are several medications for urinary incontinence on the market today mainly to help treating UUI. Therapy for OAB is focused on drugs that affect peripheral neural control mechanisms or those that act directly on bladder detrusor smooth muscle contraction, with a major emphasis on development of anticholinergic agents. These agents can inhibit the parasympathetic nerves which control bladder voiding or can exert a direct spasmolytic effect on the detrusor muscle of the bladder. This results in a decrease in intravesicular pressure, an increase in capacity and a reduction in the frequency of bladder contraction. Orally active anticholinergic drugs which are commonly prescribed, such as propantheline (ProBanthine), tolterodine tartrate (Detrol) and oxybutynin (Ditropan), have serious drawbacks such as unacceptable side effects such as dry mouth, abnormal visions, constipation, and central nervous system disturbances. These side effects lead to poor compliance. Dry mouth symptoms alone are responsible for a 70% non-compliance rate with oxybutynin. The inadequacies of present therapies highlight the need for novel, efficacious, safe, orally available drugs that have fewer side effects.

WO03/014064 discloses the compounds represented by the general formula:

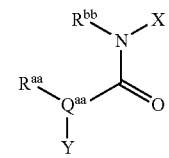

wherein

X represents $C_{3-8}$ cycloalkyl optionally fused by benzene, optionally substituted naphthyl, optionally substituted phenyl, optionally substituted phenyl $C_{1-6}$ straight alkyl, phenyl fused by cycloalykyl, etc;

$Q^{aa}$ represents CH or N;

$R^{aa}$ represents hydrogen or methyl;

$R^{bb}$ represents hydrogen or methyl; and

Y represents substituted naphthyl, as a vanilloid receptor antagonist.

WO03/022809 discloses the compounds having vanilloid receptor antagonist activity represented by the general formula:

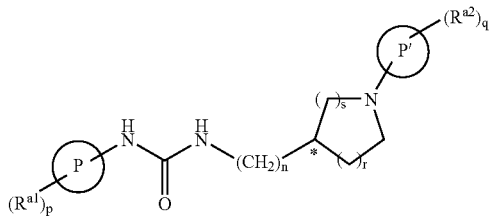

wherein
P and P' independently represent aryl or heteroaryl;
$R^{a1}$ and $R^{a2}$ independently represent hydrogen, alkoxy, hydroxy, etc;
n is 0, 1, 2 or 3; p and q are independently 0, 1, 2, 3 or 4; r is 1, 2 or 3; and s is 0, 1 or 2.

WO03/068749 discloses the compounds having vanilloid receptor antagonist activity represented by the general formula:

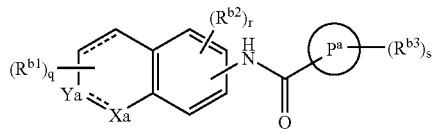

wherein
$P^a$ represents phenyl, heteroaryl or heterocyclyl;
$R^{b1}$ and $R^{b2}$ independently represent halogen, alkoxy, hydroxy, etc;
$R^{b3}$ represents alkyl, $CF_3$, alkoxy, optionally substituted phenyl, optionally substituted pyridyl etc;
q and r are independently 0, 1, 2 or 3; s is 0, 1, 2, or 3; and
Xa and Ya are selected from the following combinations;
Xa is N and Ya is $CR^{b9}$; Xa is $NR^{b8}$ and Ya is $C(R^{b9})_2$; Xa is $CR^{b9}$ and Ya is N; Xa is $C(R^{b9})_2$ and
Ya is $NR^{b8}$, wherein $R^{b8}$ and $Rb^9$ are defined in the application.

WO03/080578 discloses the compounds having vanilloid receptor antagonist activity represented by the general formula:

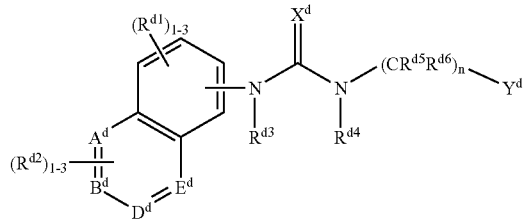

wherein
$A^d$, $B^d$, $D^d$ and $E^d$ are each C or N with the proviso that one or more are N; $X^d$ is an O, S or =NCN; $Y^d$ is an aryl, heteroaryl, carbocyclyl or fused-carbocyclyl; n is 0, 1, 2 or 3; and $R^{d1}$, $R^{d2}$, $R^{d3}$, $R^{d4}$, $R^{d5}$ and $R^{d6}$ are defined in the application.

However, none of these reference discloses hydroxy-tetrhydro-naphthalene derivatives having VR1 antagonistic activity.

The development of a compound which has effective VR1 antagonistic activity and can be used for the prophylaxis and treatment of diseases associated with VR1 activity, in particular for the treatment of urinary incontinence, urge urinary incontinence, overactive bladder as well as pain, and/or inflammatory diseases such as asthlma and COPD has been desired.

SUMMARY OF THE INVENTION

This invention is to provide compounds of the formula (I), their tautomeric and stereoisomeric form, and salts thereof:

wherein
A represents the formula

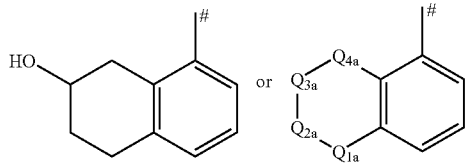

wherein
represents the connection position to the molecule
and $Q_{1a}$, $Q_{2a}$, $Q_{3a}$ and $Q_{4a}$, are defined below, and
E represents the formula

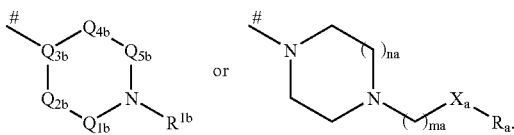

wherein
represents the connection position to the molecule
and $Q_{1b}$, $Q_{2b}$, $Q_{3b}$, $Q_{4b}$, $Q_{5b}$, $R^{1b}$, na, ma, $X_a$ and $R_a$ are defined below.

In another embodiment, the compounds of formula (I) can be hydroxy-tetrahydro-naphthalene derivatives of the formula

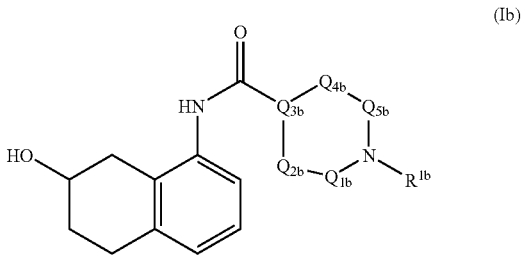

their tautomeric and stereoisomeric form, and salts thereof,
wherein
$Q_{1b}$, $Q_{2b}$, $Q_{4b}$ and $Q_{5b}$ independently represent $C(R^{11b})(R^{12b})$,
wherein
$R^{11b}$ and $R^{12b}$ independently represent hydrogen, phenyl, benzyl, or $C_{1-6}$alkyl optionally substituted by hydroxy, carboxy, phenyl, benzyl, $C_{1-6}$alkoxy, $C_{1-6}$alkoxycarbonyl, $C_{1-6}$alkylamino, or di($C_{1-6}$alkyl)amino;
$Q_{3b}$ represents C—$R^{13b}$, wherein R$^{13b}$ represents hydrogen, phenyl, benzyl, or C$_{1-6}$ alkyl optionally substituted by hydroxy, carboxy, phenyl, benzyl, C$_{1-6}$alkoxy, C$_{1-6}$alkoxycarbonyl, C$_{1-6}$alkylamino, or di(C$_{1-6}$alkyl)amino;

R$^{1b}$ represents C$_{1-6}$alkyl substituted by aryl or heteroaryl, wherein said aryl and heteroaryl are optionally substituted with one or more substituents selected from the group consisting of halogen, nitro, hydroxy, C$_{1-6}$alkylamino, di(C$_{1-6}$ alkyl)amino, C$_{3-8}$ cycloalkylamino, C$_{1-6}$ alkoxycarbonyl, phenyl, benzyl, heterocycle, sulfonamide, C$_{1-6}$ alkanoyl, C$_{1-6}$ alkanoylamino, carbamoyl, C$_{1-6}$alkylcarbamoyl, cyano, C$_{1-6}$alkyl optionally substituted by cyano, C$_{1-6}$ alkoxycarbonyl or mono-, di-, or tri-halogen, C$_{1-6}$ alkoxy optionally substituted by mono-, di-, or tri-halogen, phenoxy optionally substituted by halogen or C$_{1-6}$ alkyl, or C$_{1-6}$ alkylthio optionally substituted by mono-, di-, or tri-halogen, C$_{3-8}$ cycloalkyl, and heterocycle;

or aryl or heteroaryl, wherein said aryl and heteroaryl are optionally substituted with one or more substituents selected from the group consisting of halogen, nitro, hydroxy, C$_{1-6}$ alkylamino, di(C$_{1-6}$ alkyl)amino, C$_{3-8}$ cycloalkylamino, C$_{1-6}$ alkoxycarbonyl, phenyl, benzyl, heterocycle, sulfonamide, C$_{1-6}$ alkanoyl, C$_{1-6}$ alkanoylamino, carbamoyl, C$_{1-6}$ alkylcarbamoyl, cyano, C$_{1-6}$ alkyl optionally substituted by cyano, C$_{1-6}$ alkoxycarbonyl or mono-, di-, or tri-halogen, C$_{1-6}$ alkoxy optionally substituted by mono-, di-, or tri-halogen, phenoxy optionally substituted by halogen or C$_{1-6}$ alkyl, or C$_{1-6}$ alkylthio optionally substituted by mono-, di-, or tri halogen, C$_{3-8}$ cycloalkyl, and heterocycle.

In another embodiment, the hydroxy-tetrahydro-naphthalenylurea derivatives of formula (Ib) can be those wherein;

R$^{1b}$ represents C$_{1-2}$ alkyl substituted by phenyl, naphthyl, pyridyl, or pyrimidyl, wherein said phenyl, naphthyl, pyridyl and pyrimidyl are optionally substituted with one or more substituents selected from the group consisting of halogen, nitro, C$_{1-6}$ alkylamino, di(C$_{1-6}$ alkyl)amino, C$_{3-8}$ cycloalkylamino, C$_{1-6}$ alkoxycarbonyl, phenyl, benzyl, C$_{1-6}$ alkanoyl, C$_{1-6}$ alkanoylamino, carbamoyl, C$_{1-6}$alkylcarbamoyl, cyano, C$_{1-6}$alkyl optionally substituted by mono-, di-, or tri-halogen, C$_{1-6}$ alkoxy optionally substituted by mono-, di-, or tri-halogen, phenoxy optionally substituted by halogen or C$_{1-6}$ alkyl, or C$_{1-6}$ alkylthio optionally substituted by mono-, di-, or tri-halogen;

or phenyl, naphthyl, pyridyl, or pyrimidyl wherein said phenyl, naphthyl, pyridyl and pyrimidyl are optionally substituted with one or more substituents selected from the group consisting of halogen, nitro, C$_{1-6}$ alkylamino, di(C$_{1-6}$ alkyl)amino, C$_{3-8}$ cycloalkylamino, C$_{1-6}$ alkoxycarbonyl, phenyl, benzyl, C$_{1-6}$ alkanoyl, C$_{1-6}$ alkanoylamino, carbamoyl, C$_{1-6}$ alkylcarbamoyl, cyano, Cl6 alkyl optionally substituted by mono-, di-, or tri-halogen, C$_{1-6}$ alkoxy optionally substituted by mono-, di-, or tri-halogen, phenoxy optionally substituted by halogen or C$_{1-6}$ alkyl, or C$_{1-6}$ alkylthio optionally substituted by mono-, di-, or tri-halogen.

In another embodiment, the hydroxy-tetrahydro-naphthalenylurea derivatives of formula (Ib) can be those wherein;

R$^{1b}$ represents phenyl, pyridyl, or pyrimidyl, wherein said phenyl, pyridyl and pyrimidyl are optionally substituted with one or more substituents selected from the group consisting of halogen, nitro, C$_{1-6}$alkylamino, di(C$_{1-6}$alkyl)amino, C$_{3-8}$ cycloalkylamino, C$_{1-6}$ alkoxycarbonyl, phenyl, benzyl, C$_{1-6}$ alkanoyl, C$_{1-6}$ alkanoylamino, carbamoyl, C$_{1-6}$ alkylcarbamoyl, cyano, C$_{1-6}$ alkyl optionally substituted by mono-, di-, or tri-halogen, C$_{1-6}$ alkoxy optionally substituted by mono-, di-, or tri-halogen, phenoxy optionally substituted by halogen or C$_{1-6}$ alkyl, or C$_{1-6}$ alkylthio optionally substituted by mono-, di-, or tri-halogen.

Preferably, the hydroxy-tetrahydronaphthalene derivative of formula (Ib) are those wherein;

Q$_{1b}$, Q$_{2b}$, Q$_{4b}$ and Q$_{5b}$ represent CH$_2$;

Q$_{3b}$ represents CH;

R$^{1b}$ represents phenyl, pyridyl, or pyrimidyl wherein said phenyl, pyridyl and pyrimidyl are optionally substituted with one or more substituents selected from the group consisting of chloro, bromo, fluoro, nitro, methoxy, trifluoromethyl, trifluoromethoxy and C$_{1-6}$ alkanoylamino.

More preferably, said hydroxy-tetrahydro-naphthalene derivative of the formula (Ib) is selected from the group consisting of:

1-2-Chlorophenyl)-N-(7-hydroxy-5,6,7,8-tetrahydronaphtalen-1-yl)piperidine-4-carboxamide;

N-(7-Hydroxy-5,6,7,8-tetrahydronaphthalen-1-yl)-1-(2-nitrophenyl)piperidine-4-carboxamide;

N-(7-Hydroxy-5,6,7,8-tetrahydronaphthalen-1-yl)-1-[2-nitro(trifluoromethyl)phenyl]piperidine-4-carboxamide;

1-(2-Fluorophenyl)-N-(7-hydroxy-5,6,7,8-tetrahydronaphthalen-1-yl)piperidine-4-carboxamide;

1-(4-Fluorophenyl)-N-(7-hydroxy-5,6,7,8-tetrahydronaphthalen-1-yl)piperidine-4-carboxamide;

1-[4-Chloro-2-(trifluoromethyl)phenyl]-N-(7-hydroxy-5,6,7,8-tetrahydronaphthalen-1-yl)piperidine-4-carboxamide;

N-(7-Hydroxy-5,6,7,8-tetrahydronaphthalen-1-yl)-1-[4-(trifuoromethyl)phenyl]piperidine-4-carboxamide;

1-[2-Chloro-4-(trifluoromethyl)phenyl]-N-(7-hydroxy-5,6,7,8-tetrahydronaphthalen-1-yl)piperidine-4-carboxamide;

1-(4-Fluorophenyl)-N-[(7R)-7-hydroxy-5,6,7,8-tetrahydronaphthalen-1-yl]piperidine-4-carboxamide;

1-(4-Fluorophenyl)-N-[(7S)-7-hydroxy-5,6,7,8-tetrahydronaphthalen-1-yl]piperidine-4-carboxamide;

1-[2-Chloro-4-(trifluoromethyl)phenyl]-N-[(7R)-7-hydroxy-5,6,7,8-tetrahydronaphthalen-1-yl]piperidine-4-carboxamide;

1-[2-Chloro-4-(trifluoromethyl)phenyl]-N-[(7S)-7-hydroxy-5,6,7,8-tetrahydro-naphthalen-1-yl]piperidine-4-carboxamide;

1-[3-Chlorophenyl]-N-[(7R)-7-hydroxy-5,6,7,8-tetrahydronaphthalen-1-yl]piperidine-4-carboxamide;

N-[(7R)-7-Hydroxy-1-phenyl-5,6,7,8-tetrahydronaphthalen-1-yl]piperdine-4-carboxamide;

N-[(7R)-7-Hydroxy-5,6,7,8-tetrahydronaphthalen-1-yl]-1-[3-trifluoromethyl-phenyl]piperidine-4-carboxamide;

N-[(7R)-7-Hydroxy-5,6,7,8-tetrahydronaphthalen-1-yl]-1-[3-trifluoromethoxy-phenyl]piperidine-4-carboxamide;

1-[2,4-Dichlorophenyl]-N-[(7R)-7-hydroxy-5,6,7,8-tetrahydronaphthalen-1-yl]piperidine-4-carboxamide;

1-[3,4-Bis[trifluoromethoxy]phenyl]-N-[(7R)-7-hydroxy-5,6,7,8-tetrahydro-naphthalen-1-yl]piperidine-4-carboxamide;

N-[(7R)-7-Hydroxy-5,6,7,8-tetrahydronaphthalen-1-yl]-1-[4-trifluoromethoxy-phenyl]piperidine-4-carboxamide;

N-[(7R)-7-Hydroxy-5,6,7,8-tetrahydronaphthalen-1-yl]-1-[4-trifluoromethyl-pyrimidin-2-yl]-piperidine-4-carboxamide;

1-[5-Chloropyrimidin-2-yl]-N-[(7R)-7-hydroxy-5,6,7,8-tetrahydronaphthalen-1-yl]piperidine-4-carboxamide;

1-[2-Chloro-4-nitrophenyl]-N-[(7R)-7-hydroxy-5,6,7,8-tetrahydronaphthalen-1-yl]piperidine-4-carboxamide;

1-[3-(Acetylamino)-5-(trifluoromethyl)pyridin-2-yl]-N-[(7R)-7-hydroxy-5,6,7,8-tetrahydronaphthalen-1-yl]piperidine-4-carboxamide;

N-[(7R)-7-Hydroxy-5,6,7,8-tetrahydronaphthalen-1-yl]-1-[5-(trifluoromethyl)-pyridin-2-yl]piperidine-4-carboxamide; and N-[(7R)-7-Hydroxy-5,6,7,8-tetrahydronaphthalen-1-yl]-1-[4-trifluoromethyl-phenyl]piperidine-4-carboxamide.

In another embodiment, the compounds of formula (I) can be urea derivatives of the formula

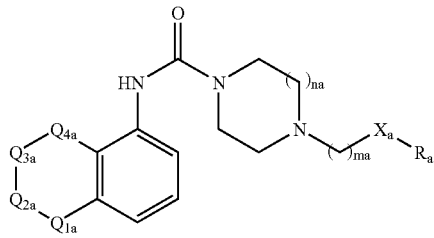

(Ia)

their tautomeric and stereoisomeric form, and salts thereof, wherein na represents 1 or 2;

ma represents 0, 1, 2, or 3;

—$X_a$— represents bond, —O— or —N($R^{1a}$)— (wherein $R^{1a}$ is hydrogen or $C_{1-6}$ alkyl);

$Q_{1a}$ and $Q_{4a}$ independently represent direct bond or methylene, $Q_{2a}$ represents CHR$^{2a}$, $Q_{3a}$ represents CHR$^{3a}$, wherein $R^{2a}$ represents hydrogen, hydroxy, $C_{1-6}$ alkoxy or $C_{1-6}$ alkanoyloxy, and $R^{3a}$ represents hydrogen, hydroxy, $C_{1-6}$ alkoxy, or $C_{1-6}$ alkanoyloxy, with the proviso that $Q_{1a}$ and $Q_{4a}$ can not be direct bond at the same time and $R^{2a}$ and $R^{3a}$ can not be hydrogen at the same time;

and $R_a$ represents aryl or heteroaryl

Wherein said aryl and heteroaryl are optionally substituted with one or more substituents independently selected from the group consisting of halogen, nitro, hydroxy, carboxy, amino, $C_{1-6}$alkylamino, di($C_{1-6}$alkyl)amino, $C_{3-8}$ cycloalkylamino, $C_{1-6}$ alkoxycarbonyl, phenyl (which phenyl is optionally substituted by halogen, nitro, hydroxy, carboxy, amino, $C_{1-6}$ alkylamino, di($C_{1-6}$ alkyl)amino, $C_{3-8}$ cycloalkylamino, or $C_{1-6}$ alkoxycarbonyl), benzyl (in which phenyl moiety is optionally substituted by halogen, nitro, hydroxy, carboxy, amino, $C_{1-6}$ alkylamino, di($C_{1-6}$ alkyl)amino, $C_{3-8}$ cycloalkylamino, or $C_{1-6}$ alkoxycarbonyl), sulfonamide, $C_{1-6}$ alkanoyl, $C_{1-6}$ alkanoylamino, carbamoyl, $C_{1-6}$ alkylcarbamoyl, cyano, $C_{1-6}$ alkyl (which alkyl is optionally substituted by cyano, nitro, hydroxy, carboxy, amino, $C_{1-6}$ alkoxycarbonyl or mono-, di-, or tri-halogen), $C_{1-6}$ alkoxy (which alkoxy is optionally substituted by mono-, di-, or tri-halogen), phenoxy (in which phenyl moiety is optionally substituted by halogen, nitro, hydroxy, carboxy, amino, $C_{1-6}$ alkylamino, di($C_{1-6}$ alkyl)amino, $C_{3-8}$ cycloalkylamino, or $C_{1-6}$ alkoxycarbonyl or $C_{1-6}$ alkyl), $C_{1-6}$ alkylthio (which alkylthio is optionally substituted by mono-, di-, or tri-halogen), $C_{3-8}$ cycloalkyl, and heterocycle.

In another embodiment, the urea derivatives of formula (Ia) can be those wherein;

na represents 1 or 2;

ma represents 0, 1, 2, or 3;

—$X_a$— represents bond, —O— or —N($R^{1a}$)— (wherein $R^{1a}$ is hydrogen or $C_{1-6}$ alkyl);

$Q_{1a}$ and $Q_{4a}$ independently represent direct bond or methylene, $Q_{2a}$ represents CHR$^{2a}$, $Q_{3a}$ represents CHR$^{3a}$, wherein $R^{2a}$ represents hydrogen, hydroxy, $C_{1-6}$alkoxy or $C_{1-6}$ alkanoyloxy, and $R^{3a}$ represents hydrogen, hydroxy, $C_{1-6}$alkoxy, or $C_{1-6}$ alkanoyloxy, with the proviso that $Q_{1a}$ and $Q_{4a}$ can not be direct bond at the same time and $R^{2a}$ and $R^{3a}$ can not be hydrogen at the same time;

$R_a$ represents phenyl, naphthyl, pyridyl, or pyrimidyl, wherein said phenyl, naphthyl, pyridyl and pyrimidyl are optionally substituted with one or more substituents independently selected from the group consisting of halogen, nitro, hydroxy, carboxy, amino, $C_{1-6}$ alkylamino, di($C_{1-6}$ alkyl)amino, $C_{3-8}$ cycloalkylamino, $C_{1-6}$ alkoxycarbonyl, phenyl (which phenyl is optionally substituted by halogen, nitro, hydroxy, carboxy, amino, $C_{1-6}$ alkylamino, di($C_{1-6}$ alkyl)amino, $C_{3-8}$ cycloalkylamino, or $C_{1-6}$ alkoxycarbonyl), benzyl (in which phenyl moiety is optionally substituted by halogen, nitro, hydroxy, carboxy, amino, $C_{1-6}$ alkylamino, di($C_{1-6}$ alkyl)amino, $C_{3-8}$ cycloalkylamino, or $C_{1-6}$ alkoxycarbonyl), sulfonamide, $C_{1-6}$ alkanoyl, $C_{1-6}$ alkanoylamino, carbamoyl, $C_{1-6}$alkylcarbamoyl, cyano, $C_{1-6}$alkyl (which alkyl is optionally substituted by cyano, nitro, hydroxy, carboxy, amino, $C_{1-6}$ alkoxycarbonyl or mono-, di-, or tri-halogen), $C_{1-6}$ alkoxy (which alkoxy is optionally substituted by mono-, di-, or tri-halogen), phenoxy (in which phenyl moiety is optionally substituted by halogen, nitro, hydroxy, carboxy, amino, $C_{1-6}$ alkylamino, di($C_{1-6}$alkyl)amino, $C_{3-8}$ cycloalkylamino, or $C_{1-6}$ alkoxycarbonyl or $C_{1-6}$ alkyl), $C_{1-6}$ alkylthio (which alkylthio is optionally substituted by mono-, di-, or tri-halogen), $C_{3-8}$ cycloalkyl, and heterocycle.

In another embodiment, the urea derivatives of formula (Ia) can be those wherein;

na represents 1 or 2;

ma represents 0, 1, 2, or 3;

—$X_a$— represents bond, —O— or —N($R^{1a}$)— (wherein $R^{1a}$ is hydrogen or $C_{1-6}$ alkyl);

$Q_{1a}$ and $Q_{4a}$ represent methylene, $Q_{2a}$ represents CHR$^{2a}$, $Q_{3a}$ represents CHR$^{3a}$, wherein $R^{2a}$ represents hydroxy, $C_{1-6}$alkoxy or $C_{1-6}$ alkanoyloxy, and $R^{3a}$ represents hydrogen;

$R_a$ represents phenyl, naphthyl, pyridyl, or pyrimidyl, wherein said phenyl, naphthyl, pyridyl and pyrimidyl are optionally substituted with one or more substituents independently selected from the group consisting of halogen, nitro, hydroxy, carboxy, amino, $C_{1-6}$ alkylamino, di($C_{1-6}$ alkyl)amino, $C_{3-8}$ cycloalkylamino, $C_{1-6}$ alkoxycarbonyl, phenyl (which phenyl is optionally substituted by halogen, nitro, hydroxy, carboxy, amino, $C_{1-6}$ alkylamino, di($C_{1-6}$ alkyl)amino, $C_{3-8}$ cycloalkylamino, or $C_{1-6}$ alkoxycarbonyl), benzyl (in which phenyl moiety is optionally substituted by halogen, nitro, hydroxy, carboxy, amino, $C_{1-6}$ alkylamino, di($C_{1-6}$ alkyl)amino, $C_{3-8}$ cycloalkylamino, or $C_{1-6}$ alkoxycarbonyl), sulfonamide, $C_{1-6}$ alkanoyl, $C_{1-6}$ alkanoylamino, carbamoyl, $C_{1-6}$ alkylcarbamoyl, cyano, $C_{1-6}$ alkyl (which alkyl is optionally substituted by cyano, nitro, hydroxy, carboxy, amino, $C_{1-6}$ alkoxycarbonyl or mono-, di-, or tri-halogen), $C_{1-6}$ alkoxy (which alkoxy is optionally substituted by mono-, di-, or tri-halogen), phenoxy (in which phenyl moiety is optionally substituted by halogen, nitro, hydroxy, carboxy, amino, $C_{1-6}$ alkylamino, di($C_{1-6}$alkyl)amino, $C_{3-8}$ cycloalkylamino, or $C_{1-6}$ alkoxycarbonyl or $C_{1-6}$ alkyl), $C_{1-6}$ alkylthio (which alkylthio is optionally substituted by mono-, di-, or tri-halogen), $C_{3-8}$ cycloalkyl, and heterocycle.

In a further embodiment, said urea derivative of the formula (Ia) can be those wherein;

na represents 1 or 2;
ma represents 0, 1, 2, or 3;
—$X_a$— represents bond, —O— or —N($R^{1a}$)— (wherein $R^{1a}$ is hydrogen or $C_{1-6}$ alkyl);
$Q_{1a}$ and $Q_{4a}$ represent methylene,
$Q_{2a}$ represents CHR$^2$,
$Q_{3a}$ represents CHR$^3$, wherein $R^{2a}$ represents hydrogen; and
$R^{3a}$ represents hydroxy, $C_{1-6}$ alkoxy or $C_{1-6}$ alkanoyloxy;
$R_a$ represents phenyl, naphthyl, pyridyl, or pyrimidyl, wherein said phenyl, naphthyl, pyridyl and pyrimidyl are optionally substituted with one or more substituents independently selected from the group consisting of halogen, nitro, hydroxy, carboxy, amino, $C_{1-6}$ alkylamino, di($C_{1-6}$ alkyl)amino, $C_{3-8}$ cycloalkylamino, $C_{1-6}$ alkoxycarbonyl, phenyl (which phenyl is optionally substituted by halogen, nitro, hydroxy, carboxy, amino, $C_{1-6}$ alkylamino, di($C_{1-6}$ alkyl)amino, $C_{3-8}$ cycloalkylamino, or $C_{1-6}$ alkoxycarbonyl), benzyl (in which phenyl moiety is optionally substituted by halogen, nitro, hydroxy, carboxy, amino, $C_{1-6}$ alkylamino, di($C_{1-6}$ alkyl)amino, $C_{3-8}$ cycloalkylamino, or $C_{1-6}$ alkoxycarbonyl), sulfonamide, $C_{1-6}$ alkanoyl, $C_{1-6}$ alkanoylamino, carbamoyl, $C_{1-6}$ alkylcarbamoyl, cyano, $C_{1-6}$ alkyl (which alkyl is optionally substituted by cyano, nitro, hydroxy, carboxy, amino, $C_{1-6}$ alkoxycarbonyl or mono-, di-, or tri-halogen), $C_{1-6}$ alkoxy (which alkoxy is optionally substituted by mono-, di-, or tri-halogen), phenoxy (in which phenyl moiety is optionally substituted by halogen, nitro, hydroxy, carboxy, amino, $C_{1-6}$ alkylamino, di($C_{1-6}$alkyl)amino, $C_{3-8}$ cycloalkylamino, or $C_{1-6}$ alkoxycarbonyl or $C_{1-6}$ alkyl), $C_{1-6}$ alkylthio (which alkylthio is optionally substituted by mono-, di-, or tri-halogen), $C_{3-8}$ cycloalkyl, and heterocycle.

Yet in a further embodiment, said urea derivative of the formular (Ia) can be those wherein:

na represents 1 or 2;
ma represents 0, 1, 2, or 3;
—$X_a$— represents bond, —O— or —N($R^{1a}$)— (wherein $R^{1a}$ is hydrogen or $C_{1-6}$ alkyl);
$Q_{1a}$ and $Q_{4a}$ represent methylene,
$Q_{2a}$ represents CHR$^{2a}$,
$Q_{3a}$ represents CHR$^{3a}$, wherein $R^{2a}$ represents hydrogen, and
$R^{3a}$ represents hydroxy;
$R_a$ represents phenyl, naphthyl, pyridyl, or pyrimidyl, wherein said phenyl, naphthyl, pyridyl and pyrimidyl are optionally substituted with one or more substituents independently selected from the group consisting of halogen, nitro, hydroxy, carboxy, amino, $C_{1-6}$ alkylamino, di($C_{1-6}$ alkyl)amino, $C_{3-8}$ cycloalkylamino, $C_{1-6}$ alkoxycarbonyl, phenyl (which phenyl is optionally substituted by halogen, nitro, hydroxy, carboxy, amino, $C_{1-6}$ alkylamino, di($C_{1-6}$ alkyl)amino, $C_{3-8}$ cycloalkylamino, or $C_{1-6}$ alkoxycarbonyl), benzyl (in which phenyl moiety is optionally substituted by halogen, nitro, hydroxy, carboxy, amino, $C_{1-6}$ alkylamino, di($C_{1-6}$ alkyl)amino, $C_{3-8}$ cycloalkylamino, or $C_{1-6}$ alkoxycarbonyl), sulfonamide, $C_{1-6}$ alkanoyl, $C_{1-6}$ alkanoylamino, carbamoyl, $C_{1-6}$ alkylcarbamoyl, cyano, $C_{1-6}$ alkyl (which alkyl is optionally substituted by cyano, nitro, hydroxy, carboxy, amino, $C_{1-6}$ alkoxycarbonyl or mono-, di-, or tri-halogen), $C_{1-6}$ alkoxy (which alkoxy is optionally substituted by mono-, di-, or tri-halogen), phenoxy (in which phenyl moiety is optionally substituted by halogen, nitro, hydroxy, carboxy, amino, $C_{1-6}$ alkylamino, di($C_{1-6}$alkyl)amino, $C_{3-8}$ cycloalkylamino, or $C_{1-6}$ alkoxycarbonyl or $C_{1-6}$ alkyl), $C_{1-6}$ alkylthlo (which alkylthlo is optionally substituted by mono-, di-, or tri-halogen), $C_{3-8}$ cycloalkyl, and heterocycle.

In a further embodiment, said urea derivative of the formular (Ia) can be those wherein:

na represents 1 or 2;
ma represents 0, 1, 2, or 3
—$X_a$— represents bond;
$Q_{1a}$ and $Q_{4a}$ represent methylene,
$Q_{2a}$ represents CHR$^{2a}$,
$Q_{3a}$ represents CHR$^{3a}$, wherein $R^{2a}$ represents hydrogen and
$R^{3a}$ represents hydroxy, $C_{1-6}$ alkoxy or $C_{1-6}$ alkanoyloxy;
$R_a$ represents phenyl, naphthyl, pyridyl, or pyrimidyl, wherein said phenyl, naphthyl, pyridyl and pyrimidyl are optionally substituted with one or more substituents independently selected from the group consisting of halogen, nitro, hydroxy, carboxy, amino, $C_{1-6}$ alkylamino, di($C_{1-6}$ alkyl)amino, $C_{3-8}$ cycloalkylamino, $C_{1-6}$ alkoxycarbonyl, phenyl (which phenyl is optionally substituted by halogen, nitro, hydroxy, carboxy, amino, $C_{1-6}$ alkylamino, di($C_{1-6}$alkyl)amino, $C_{3-8}$ cycloalkylamino, or $C_{1-6}$ alkoxycarbonyl), benzyl (in which phenyl moiety is optionally substituted by halogen, nitro, hydroxy, carboxy, amino, $C_{1-6}$ alkylamino, di($C_{1-6}$ alkyl)amino, $C_{3-8}$ cycloalkylamino, or $C_{1-6}$ alkoxycarbonyl), sulfonamide, $C_{1-6}$ alkanoyl, $C_{1-6}$ alkanoylamino, carbamoyl, $C_{1-6}$alkylcarbamoyl, cyano, $C_{1-6}$alkyl (which alkyl is optionally substituted by cyano, nitro, hydroxy, carboxy, amino, $C_{1-6}$ alkoxycarbonyl or mono-, di-, or tri-halogen), $C_{1-6}$ alkoxy (which alkoxy is optionally substituted by mono-, di-, or tri-halogen), phenoxy (in which phenyl moiety is optionally substituted by halogen, nitro, hydroxy, carboxy, amino, $C_{1-6}$ alkylamino, di($C_{1-6}$ alkyl)amino, $C_{3-8}$ cycloalkylamino, or $C_{1-6}$ alkoxycarbonyl or $C_{1-6}$ alkyl), $C_{1-6}$ alkylthio (which alkylthio is optionally substituted by mono-, di-, or tri-halogen), $C_{3-8}$ cycloalkyl, and heterocycle.

Yet in a further embodiment, said urea derivative of the formular (Ia) can be those wherein:
na represents 1 or 2;
ma represents 1, 2, or 3;
—$X_a$— represents —O— or —N($R^{1a}$)— (wherein $R^{1a}$ is hydrogen or $C_{1-6}$ alkyl);
$Q_{1a}$ and $Q_{4a}$ represent methylene,
$Q_{2a}$ represents $CHR^{2a}$,
$Q_{3a}$ represents $CHR^{3a}$, wherein
$R^{2a}$ represents hydrogen and
$R^{3a}$ represents hydroxy, $C_{1-6}$ alkoxy or $C_{1-6}$ alkanoyloxy;
$R_a$ represents phenyl, naphthyl, pyridyl, or pyrimidyl wherein said phenyl, naphthyl, pyridyl and pyrimidyl are optionally substituted with one or more substituents independently selected from the group consisting of halogen, nitro, hydroxy, carboxy, amino, $C_{1-6}$ alkylamino, di($C_{1-6}$ alkyl)amino, $C_{3-8}$ cycloalkylamino, $C_{1-6}$ alkoxycarbonyl, phenyl (which phenyl is optionally substituted by halogen, nitro, hydroxy, carboxy, amino, $C_{1-6}$ alkylamino, di($C_{1-6}$ alkyl)amino, $C_{3-8}$ cycloalkylamino, or $C_{1-6}$ alkoxycarbonyl), benzyl (in which phenyl moiety is optionally substituted by halogen, nitro, hydroxy, carboxy, amino, $C_{1-6}$ alkylamino, di($C_{1-6}$ alkyl)amino, $C_{3-8}$ cycloalkylamino, or $C_{1-6}$ alkoxycarbonyl), sulfonamide, $C_{1-6}$ alkanoyl, $C_{1-6}$ alkanoylamino, carbamoyl, $C_{1-6}$ alkylcarbamoyl, cyano, $C_{1-6}$alkyl (which alkyl is optionally substituted by cyano, nitro, hydroxy, carboxy, amino, $C_{1-6}$ alkoxycarbonyl or mono-, di-, or tri-halogen), $C_{1-6}$ alkoxy (which alkoxy is optionally substituted by mono-, di-, or tri-halogen), phenoxy (in which phenyl moiety is optionally substituted by halogen, nitro, hydroxy, carboxy, amino, $C_{1-6}$ alkylamino, di($C_{1-6}$ alkyl)amino, $C_{3-8}$ cycloalkylamino, or $C_{1-6}$ alkoxycarbonyl or $C_{1-6}$ alkyl), $C_{1-6}$ alkylthio (which alkylthio is optionally substituted by mono-, di-, or tri-halogen), $C_{3-8}$ cycloalkyl, and heterocycle.

Yet in a further embodiment, said urea derivative of the formular (Ia) can be those wherein:
na represents 1 or 2;
ma represents 0, 1, 2, or 3;
—$X_a$— represents bond, —O— or —N($R^{1a}$)— (wherein $R^{1a}$ is hydrogen or $C_{1-6}$ alkyl);
$Q_{1a}$ and $Q_{4a}$ represent methylene,
$Q_{2a}$ represents $CHR^{2a}$,
$Q_{3a}$ represents $CHR^{3a}$, wherein
$R^{2a}$ represents hydrogen and
$R^{3a}$ represents hydroxy, $C_{1-6}$ alkoxy or $C_{1-6}$ alkanoyloxy;
$R_a$ represents phenyl, naphthyl, pyridyl, or pyrimidyl, Wherein said phenyl, naphthyl, pyridyl, or pyrimidyl is optionally substituted by one or more of substituents selected from the group consisting of chloro, bromo, fluoro, nitro, methoxy, trifluoromethyl, trifluoromethoxy and $C_{1-6}$ alkanoylamino.

Preferably, said urea derivative of the formula (Ia) is selected from the group consisting of:
4-(2-chlorophenyl)-N-(7-hydroxy-5,6,7,8-tetydronaphthalen-1-yl)piperazine-1-carboxamide;
N-(7-hydroxy-5,6,7,8-tetrahydronaphthalen-1-yl)-4-[3-(trifluoromethyl)pyridin-2-yl]piperazine-1-carboxamide;
4-cyclohexyl-N-(7-hydroxy-5,6,7,8-tetrahydronaphthalen-1-yl)piperazine-1-carboxamide; and the salts thereof.

The compounds of formula (I), their tautomeric and stereoisomeric form, and salts thereof surprisingly show excellent VR1 antagonistic activity. They are, therefore suitable especially for the prophylaxis and treatment of diseases associated with VR1 activity, in particular for the treatment of urological diseases or disorders, such as detrusor overactivity (overactive bladder), urinary incontinence, neurogenic detrusor oeractivity (detrusor hyperflexia), idiopathic detrusor overactivity (detrusor instability), benign prostatic hyperplasia, and lower urinary tract symptoms.

The compounds of the present invention are also effective for treating or preventing a disease selected from the group consisting of chronic pain, neuropathic pain, postoperative pain, rheumatoid arthritic pain, neuralgia, neuropathies, algesia, nerve injury, ischaemia, neurodegeneration and/or stroke, as well as inflammatory diseases such as asthma and COPD since the diseases also relate to VR1 activity.

The compounds of the present invention are also useful for the treatment and prophylaxis of neuropathic pain, which is a form of pain often associated with herpes zoster and post-herpetic neuralgia, painful diabetic neuropathy, neuropathic low back pain, posttraumatic and postoperative neuralgia, neuralgia due to nerve compression and other neuralgias, phantom pain, complex regional pain syndromes, infectious or parainfectious neuropathies like those associated with HIV infection, pain associated with central nervous system disorders like multiple sclerosis or Parkinson disease or spinal cord injury or traumatic brain injury, and post-stroke pain.

Furthermore, the compounds of the present invention are useful for the treatment of musculoskeletal pain, forms of pain often associated with osteoarthritis or rheumatoid arthritis or other forms of arthritis, and back pain.

In addition, the compounds of the present invention are useful for the treatment of pain associated with cancer, including visceral or neuropathic pain associated with cancer or cancer treatment.

The compounds of the present invention are furthermore useful for the treatment of visceral pain, e.g. pain associated with obstruction of hollow viscus like gallstone colik, pain associated with irritable bowel syndrome, pelvic pain, vulvodynia, orchialgia or prostatodynia, pain associated with inflammatory lesions of joints, skin, muscles or nerves, and orofascial pain and headache, e.g. migraine or tension-type headache.

Further, the present invention provides a medicament, which includes one of the compounds, described above and optionally pharmaceutically acceptable excipients.

Alkyl per se and "alk" and "alkyl" in alkenyl, alkynyl, alkoxy, alkanoyl, alkylamino, alkylaminocarbonyl, alkylaminosulfonyl, alkylsulfonylamino, alkoxycarbonyl, alkoxycarbonylamino and alkanoylamino represent a linear or branched alkyl radical having generally 1 to 6, preferably 1 to 4 and particularly preferably 1 to 3 carbon atoms, representing illustratively and preferably methyl, ethyl, n-propyl, isopropyl, tert-butyl, n-pentyl and n-hexyl.

Alkoxy illustratively and preferably represents methoxy, ethoxy. n-propoxy, isopropoxy, tert-butoxy, n-pentoxy and n-hexoxy.

Alkylamino illustratively and preferably represents an alkylamino radical having one or two (independently selected) alkyl substituents, illustratively and preferably representing methylamino, ethylamino, n-propylamino, isopropylamino, tert-butylamino, n-pentylamino, n-hexyl-amino, N,N-dimethylamino, N,N-diethylamino, N-ethyl-N-methylamino, N-methyl-N-n-propylamino, N-isopropyl-N-n-propylamino, N-tert-butyl-N-methylamino, N-ethyl-N-n-pentylamino and N-n-hexyl-N-methylamino.

Cycloalkyl per se and in cycloalkylamino and in cycloalkylcarbonyl represents a cycloalkyl group having generally 3 to 8 and preferably 5 to 7 carbon atoms, illustratively and preferably representing cyclopropyl, cyclobutyl, cyclopentyl, cyclohexyl and cycloheptyl.

Heterocyclyl per se and in heterocylylcarbonyl represents a mono- or polycyclic, preferably mono- or bicyclic, nonaromatic heterocyclic radical having generally 4 to 10 and preferably 5 to 8 ring atoms and up to 3 and preferably up to 2 hetero atoms and/or hetero groups selected from the group consisting of N, O, S, SO and $SO_2$. The heterocyclyl radicals can be saturated or partially unsaturated. Preference is given to 5- to 8-membered monocyclic saturated heterocyclyl radicals having up to two hetero atoms selected from the group consisting of O, N and S, such as illustratively and preferably tetrahydrofuran-2-yl, pyrrolidin-2-yl, pyrrolidin-3-yl, pyrrolinyl, piperidinyl, morpholinyl, perhydroazepinyl.

Aryl per se and in arylamino and in arylcarbonyl represents a mono- to tricyclic aromatic carbocyclic radical having generally 6 to 14 carbon atoms, illustratively and preferably representing phenyl, naphthyl and phenanthrenyl.

Heteroaryl per se and in heteroarylamino and heteroarylcarbonyl represents an aromatic mono- or bicyclic radical having generally 5 to 10 and preferably 5 or 6 ring atoms and up to 5 and preferably up to 4 hetero atoms selected from the group consisting of S, O and N, illustratively and preferably representing thienyl, furyl, pyrrolyl, thiazolyl, oxazolyl, imidazolyl, pyridyl, pyrimidyl, pyridazinyl, indolyl, indazolyl, benzofuranyl, benzothiophenyl, quinolinyl, isoquinolinyl.

EMBODIMENT OF THE INVENTION

The compound of the formula (I) of the present invention can be, but not limited to be, prepared by combining various known methods. In some embodiments, one or more of the substituents, such as amino group, carboxyl group, and hydroxyl group of the compounds used as starting materials or intermediates are advantageously protected by a protecting group known to those skilled in the art. Examples of the protecting groups are described in "Protective Groups in Organic Synthesis (3rd Edition)" by Greene and Wuts, John Wiley and Sons, New York 1999.

The general formula (I) contains the compounds of the formula (Ia) and the compounds of the formula (Ib).

The compound of the formula (I) of the present invention can be, but not limited to be, prepared by the Method [Ab] or Method [Aa] to [Da] below.

[Method Ab]

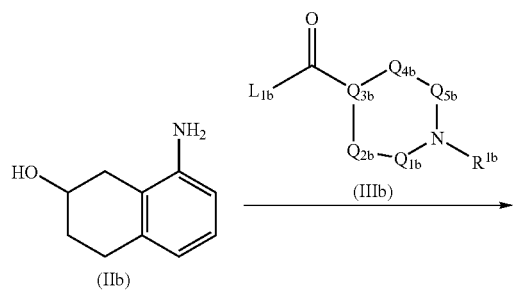

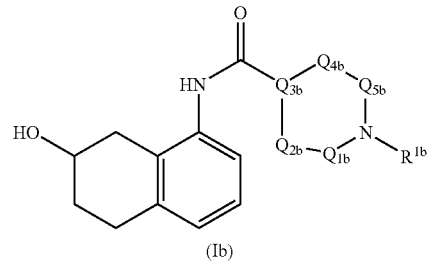

The compound of the formula (Ib) (wherein $Q_{1b}$, $Q_{2b}$, $Q_{3b}$, $Q_{4b}$, $Q_{5b}$ and $R^{1b}$ are the same as defined) can be prepared by the reaction of the compound of the formula (IIb) with the compound of the formula (IIIb) (wherein $Q_{1b}$, $Q_{2b}$, $Q_{3b}$, $Q_{4b}$, $Q_{5b}$ and $R^{1b}$ are the same as defined above and $L_{1b}$ represents a leaving group including, for instance, hydroxy, halogen atom such as chlorine, bromine, or iodine atom, or azole such as imidazole or triazole.).

The reaction may be carried out in a solvent including, for instance, halogenated hydrocarbons such as dichloromethane, chloroform and 1,2-dichloroethane; ethers such as diethyl ether, isopropyl ether, dioxane and tetrahydrofuran (THF) and 1,2-dimethoxyethane; aromatic hydrocarbons such as benzene, toluene and xylene; nitriles such as acetonitrile; amides such as N,N-dimethylformamide (DMF), N,N-dimethylacetamide (DMAC) and N-methylpyrrolidone (NMP); ureas such as 1,3-dimethyl-2-imidazolidinone (DMI); sulfoxides such as dimethylsulfoxide (DMSO); and others. Optionally, two or more of the solvents selected from the listed above can be mixed and used.

The reaction temperature can be optionally set depending or the compounds to be reacted. The reaction temperature is usually, but not limited to, about 0° C. to 50° C. The reaction may be conducted for, usually, 30 minutes to 10 hours and preferably 1 to 24 hours.

The reaction can be advantageously carried out in the presence of a base including, for instance, organic amines such as pyridine, triethylamine and N,N-diisopropylethylamine, dimethylaniline, diethylaniline, 4-dimethylaminopyridine, and others.

When $L_{1b}$ is hydroxy, the reaction can be advantageously carried out using coupling agent including, for instance, hydroxybenzotriazole, carbodiimides such as N,N-dicyclohexylcarbodiimide and 1-(3-dimethyl-aminopropyl)-3-ethylcarbodiimide; carbonyldiazoles such as 1,1'-carbonyldi(1,3-imiazole)(CDI) and 1,1'-carbonyldi(1,2,4-triazole)(CDT), and the like.

The compound (IIb) and (IIIb) are commercially available or can be prepared by the use of known techniques.

[Method Aa]

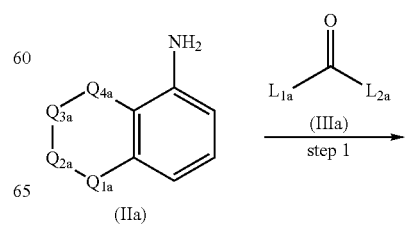

-continued

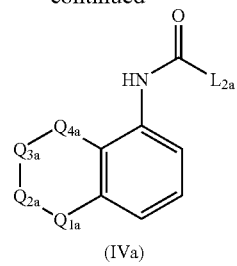

(IVa)

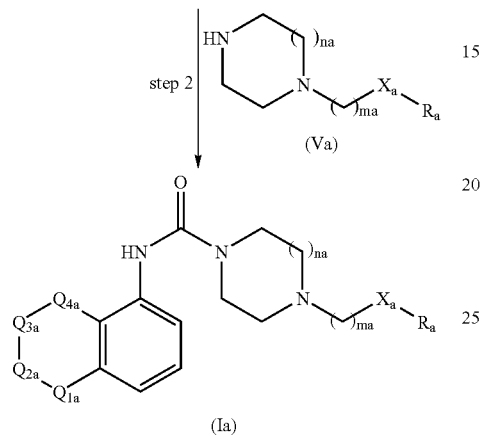

The compound of the formula (IVa) (wherein $Q_{1a}$, $Q_{2a}$, $Q_{3a}$, and $Q_{4a}$ are the same as defined) can be prepared by the reaction of the compound of the formula (IIa) (wherein $Q_{1a}$, $Q_{2a}$, $Q_{3a}$, and $Q_{4a}$ are the same as defined) with the compound of the formula (IIIa) (wherein $L_{1a}$ represents a leaving group including, for instance, hydroxy, halogen atom such as chlorine, bromine, or iodine atom, or azole such as imidazole or triazole and $L_{2a}$ represents a leaving group including, for instance, halogen atom such as chlorine, bromine, or iodine atom, or phenoxy). Then the compound of the formula (Va) (wherein na, ma, $X_a$ and $R_a$ are the same as defined) is reacted with the compound (IVa) to obtain the compound of the formula (Ia) (wherein $Q_{1a}$, $Q_{2a}$, $Q_{3a}$, $Q_{4a}$, na, ma, $X_a$ and $R_a$ are the same as defined above).

The reaction may be carried out in a solvent including, for instance, halogenated hydrocarbons such as dichloromethane, chloroform and 1,2-dichloroethane; ethers such as diethyl ether, isopropyl ether, dioxane and tetrahydrofuran (THF) and 1,2-dimethoxyethane; aromatic hydrocarbons such as benzene, toluene and xylene; nitriles such as acetonitrile; amides such as N,N-dimethylformamide (DMF), N,N-dimethylacetamide (DMAC) and N-methylpyrrolidone (NMP); ureas such as 1,3-dimethyl-2-imidazolidinone (DMI); sulfoxides such as dimethylsulfoxide (DMSO); and others. Optionally, two or more of the solvents selected from the listed above can be mixed and used.

The reaction temperature can be optionally set depending on the compounds to be reacted. The reaction temperature is usually, but not limited to, about 0° C. to 50° C. The reaction may be conducted for, usually, 30 minutes to 24 hours and preferably 1 to 10 hours.

The reaction can be advantageously carried out in the presence of a base including, for instance. organic amines such as pyridine, triethylamine and N,N-diisopropylethylamine, dimethylaniline, diethylaniline, 4-dimethylaminopyridine, and others.

When $L_{1a}$ is hydroxy, the reaction can be advantageously carried out using coupling agent including, for instance, hydroxybenzotriazole, carbodiimides such as N,N-dicyclohexylcarbodiimide and 1-(3-dimethyl-aminopropyl)-3-ethylcarbodiimide; carbonyldiazoles such as 1,1'-carbonyldi(1,3-imiazole)(CDI) and 1,1'-carbonyldi(1,2,4-triazole)(CDT), and the like.

The compound (IIa), (IIIa), and (Va) are commercially available or can be prepared by the use of known techniques.

[Method Ba]

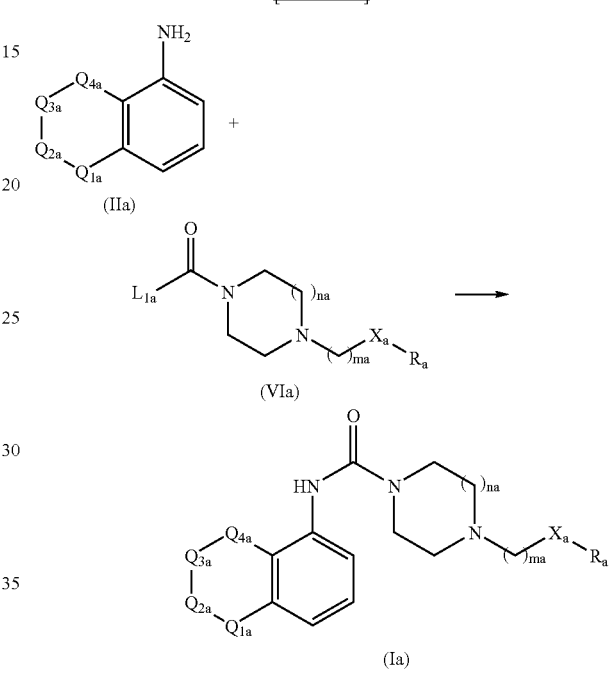

The compound of the formula (Ia) can be prepared by the reaction of the compound of the formula (IIa) and the compound of the formula (VIa) (wherein na, ma, $X_a$, $R_a$ and $L_{1a}$ are the same as defined above).

The reaction may be carried out in a solvent including, for instance, halogenated hydrocarbons such as dichloromethane, chloroform and 1,2-dichloroethane; ethers such as diethyl ether, isopropyl ether, dioxane and tetrahydrofuran (THF) and 1,2-dimethoxyethane; aromatic hydrocarbons such as benzene, toluene and xylene; nitriles such as acetonitrile; amides such as N,N-dimethylformamide (DMF), N,N-dimethylacetamide (DMAC) and N-methylpyrrolidone (NMP); urea such as 1,3-dimethyl-2-imidazolidinone (DMI); sulfoxides such as dimethylsulfoxide (DMSO); and others. Optionally, two or more of the solvents selected from the listed above can be mixed and used.

The reaction can be carried out in the presence of organic base such as pyridine or triethylamine.

The reaction temperature can be optionally set depending on the compounds to be reacted. The reaction temperature is usually, but not limited to, about room temperature to 100° C. The reaction may be conducted for, usually, 30 minutes to 48 hours and preferably 1 to 24 hours.

The compound (IIa) and (IVa) can be prepared by the use of known techniques or are commercially available.

[Method Ca]

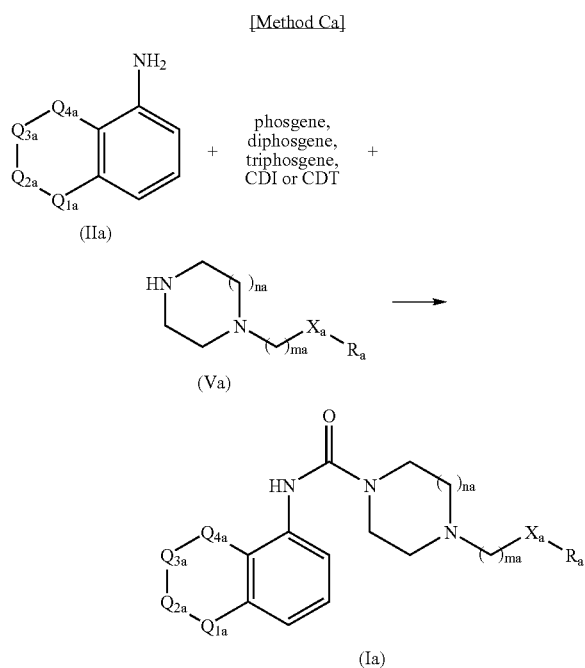

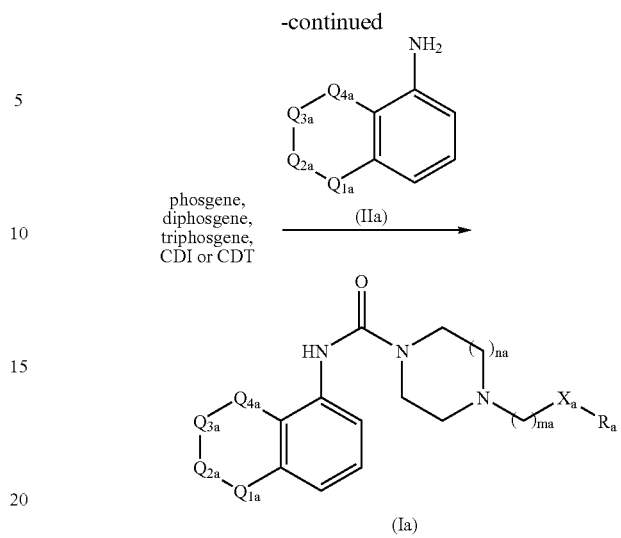

The compound of the formula (Ia) can be prepared by reacting the compound of the formula (IIa) with phosgene, diphosgene, triphosgene, 1,1-carbonyldiimidazole (CDI), or 1,1'-carbonyldi(1,2,4-triazole)(CDT), and then adding the compound of the formula (Va) to the reaction mixture.

The reaction may be carried out in a solvent including, for instance, halogenated hydrocarbons such as dichloromethane, chloroform and 1,2-dichloroethane; ethers such as diethyl ether, isopropyl ether, dioxane and tetrahydrofuran (THF) and 1,2-dimethoxyethane; aromatic hydrocarbons such as benzene, toluene and xylene; nitrites such as acetonitrile; amides such as N,N-dimethylformamide (DMF), N,N-dimethylacetamide (DMAC) and N-methylpyrrolidone (NMP); urea such as 1,3-dimethyl-2-imidazolidinone (DMI); sulfoxides such as dimethylsulfoxide (DMSO); and others. Optionally, two or more of the solvents selected from the listed above can be mixed and used.

The reaction temperature can be optionally set depending on the compounds to be reacted. The reaction temperature is usually, but not limited to, about 20° C. to 50° C. The reaction may be conducted for, usually, 30 minutes to 24 hours and preferably 1 to 10 hours.

Phosgene, diphosgene, triphosgene, CDI, and CDT are commercially available.

[Method Da]

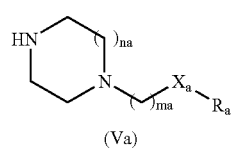

The compound of the formula (Ia) can be prepared by reacting the compound of the formula (Va) with phosgene, diphosgene, triphosgene, 1,1-carbonyldiimidazole (CDI), or 1,1'-carbonyldi(1,2,4-triazole)(CDT) and then adding the compound of the formula (IIa) to the reaction mixture.

The reaction may be carried out in a solvent including, for instance, halogenated hydrocarbons such as dichloromethane, chloroform and 1,2-dichloroethane; ethers such as diethyl ether, isopropyl ether, dioxane and tetrahydrofuran (THF) and 1,2-dimethoxyethane; aromatic hydrocarbons such as benzene, toluene and xylene; nitriles such as acetonitrile; amides such as N,N-dimethylformamide (DMF), N,N-dimethylacetamide (DMAC) and N-methylpyrrolidone (NMP); urea such as 1,3-dimethyl-2-imidazolidinone (DMI); sulfoxides such as dimethylsulfoxide (DMSO); and others. Optionally, two or more of the solvents selected from the listed above can be mixed and used.

The reaction temperature can be optionally set depending on the compounds to be reacted. The reaction temperature is usually, but not limited to, about 20° C. to 50° C. The reaction may be conducted for, usually, 30 minutes to 24 hours and preferably 1 to 10 hours.

When the compound shown by the formula (I) or a salt thereof has an asymmetric carbon in the structure, their optically active compounds and racemic mixtures are also included in the scope of the present invention.

Typical salts of the compound shown by the formula (I) include salts prepared by reaction of the compounds of the present invention with a mineral or organic acid, or an organic or inorganic base. Such salts are known as acid addition and base addition salts, respectively.

Acids to form acid addition salts include inorganic acids such as, without limitation, sulfuric acid, phosphoric acid, hydrochloric acid, hydrobromic acid, hydriodic acid and the like, and organic acids, such as, without limitation, p-toluenesulfonic acid, methanesulfonic acid, oxalic acid, p-bromophenylsulfonic acid, carbonic acid, succinic acid, citric acid, benzoic acid, acetic acid, and the like.

Base addition salts include those derived from inorganic bases, such as, without limitation, ammonium hydroxide, alkaline metal hydroxide, alkaline earth metal hydroxides, carbonates, bicarbonates, and the like, and organic bases, such as, without limitation, ethanolamine, triethylamine, tris(hydroxymethyl)aminomethane, and the like. Examples of inorganic bases include sodium hydroxide, potassium hydroxide, potassium carbonate, sodium carbonate, sodium bicarbonate, potassium bicarbonate, calcium hydroxide, calcium carbonate, and the like.

The compound of the present invention or a salt thereof, depending on its substituents, may be modified to form lower alkylesters or known other esters; and/or hydrates or other solvates. Those esters, hydrates, and solvates are included in the scope of the present invention.

The compound of the present invention may be administered in oral forms, such as, without limitation normal and enteric coated tablets, capsules, pills, powders, granules, elixirs, tinctures, solution, suspensions, syrups, solid and liquid aerosols and emulsions. They may also be administered in parenteral forms, such as, without limitation, intravenous, intraperitoneal, subcutaneous, intramuscular, and the like forms, well-known to those of ordinary skill in the pharmaceutical arts. The compounds of the present invention can be administered in intranasal form via topical use of suitable intranasal vehicles, or via transdermal routes, using transdermal delivery systems well-known to those of ordinary skilled in the art.

The dosage regimen with the use of the compounds of the present invention is selected by one of ordinary skill in the arts, in view of a variety of factors, including, without limitation, age, weight, sex, and medical condition of the recipient, the severity of the condition to be treated, the route of administration, the level of metabolic and excretory function of the recipient, the dosage form employed, the particular compound and salt thereof employed.

The compounds of the present invention are preferably formulated prior to administration together with one or more pharmaceutically-acceptable excipients. Excipients are inert substances such as, without limitation carriers, diluents, flavoring agents, sweeteners, lubricants, solubilizers, suspending agents, binders, tablet disintegrating agents and encapsulating material.

Yet another embodiment of the present invention is pharmaceutical formulation comprising a compound of the invention and one or more pharmaceutically-acceptable excipients that are compatible with the other ingredients of the formulation and not deleterious to the recipient thereof. Pharmaceutical formulations of the invention are prepared by combining a therapeutically effective amount of the compounds of the invention together with one or more pharmaceutically-acceptable excipients therefore. In making the compositions of the present invention, the active ingredient may be mixed with a diluent, or enclosed within a carrier, which may be in the form of a capsule, sachet, paper, or other container. The carrier may serve as a diluent, which may be solid, semi-solid, or liquid material which acts as a vehicle, or can be in the form of tablets, pills powders, lozenges, elixirs, suspensions, emulsions, solutions, syrups, aerosols, ointments, containing, for example, up to 10% by weight of the active compound, soft and hard gelatin capsules, suppositories, sterile injectable solutions and sterile packaged powders.

For oral administration, the active ingredient may be combined with an oral, and non-toxic, pharmaceutically-acceptable carrier, such as, without limitation, lactose, starch, sucrose, glucose, sodium carbonate, mannitol, sorbitol, calcium carbonate, calcium phosphate, calcium sulfate, methyl cellulose, and the like; together with, optionally, disintegrating agents, such as, without limitation, maize, starch, methyl cellulose, agar bentonite, xanthan gum, alginic acid, and the like; and optionally, binding agents, for example, without limitation, gelatin, natural sugars, beta-lactose, corn sweeteners, natural and synthetic gums, acacia, tragacanth, sodium alginate, carboxymethylcellulose, polyethylene glycol, waxes, and the like; and, optionally, lubricating agents, for example, without limitation, magnesium stearate, sodium stearate, stearic acid, sodium oleate, sodium benzoate, sodium acetate, sodium chloride, talc, and the like.

In powder forms, the carrier may be a finely divided solid which is in admixture with the finely divided active ingredient. The active ingredient may be mixed with a carrier having binding properties in suitable proportions and compacted in the shape and size desired to produce tablets. The powders and tablets preferably contain from about 1 to about 99 weight percent of the active ingredient which is the novel composition of the present invention. Suitable solid carriers are magnesium carboxymethyl cellulose, low melting waxes, and cocoa butter.

Sterile liquid formulations include suspensions, emulsions, syrups and elixirs. The active ingredient can be dissolved or suspended in a pharmaceutically acceptable carriers, such as sterile water, sterile organic solvent, or a mixture of both sterile water and sterile organic solvent.

The active ingredient can also be dissolved in a suitable organic solvent, for example, aqueous propylene glycol. Other compositions can be made by dispersing the finely divided active ingredient in aqueous starch or sodium carboxymethyl cellulose solution or in a suitable oil.

The formulation may be in unit dosage form, which is a physically discrete unit containing a unit dose, suitable for administration in human or other mammals. A unit dosage form can be a capsule or tablets, or a number of capsules or tablets. A "unit dose" is a predetermined quantity of the active compound of the present invention, calculated to produce the desired therapeutic effect, in association with one or more excipients. The quantity of active ingredient in a unit dose may be varied or adjusted from about 0.1 to about 1000 milligrams or more according to the particular treatment involved.

Typical oral dosages of the present invention, when used for the indicated effects, will range from about 0.01 mg/kg/day to about 100 mg/kg/day preferably from 0.1 mg/kg/day to 30 mg/kg/day, and most preferably from about 0.5 mg/kg/day to about 10 mg/kg/day. In the case of parenteral administration, it has generally proven advantageous to administer quantities of about 0.001 to 100 mg/kg/day, preferably from 0.01 mg/kg/day to 1 mg/kg/day. The compounds of the present invention may be administered in a single daily dose, or the total daily dose may be administered in divided doses, two, three, or more times per day. Where delivery is via transdermal forms, of course, administration is continuous.

EXAMPLES

The present invention will be described as a form of examples, but they should by no means be construed as defining the metes and bounds of the present invention.

In the examples below, all quantitative data, if not stated otherwise, relate to percentages by weight.

The Following Abbreviations Are Used in the Descriptions:
appx.=approximately
aq.=aqueous
DMSO=dimethyl sufoxide
eq.=equivalent
HPLC=High Pressure Liquid Chromatography
LCMS=Liquid Chromatography coupled with Mass Spectroscopy
min.=minute
MS=Mass Spectroscopy RP-HPLC=Reverse Phase High Pressure Liquid Chromatography $R_t$=retention time TLC=Thin Layer Chromatography HPLC- and LCMS-Methods:

Method A (HPLC): instrument: HP 1100 with DAD-detektion; column: Kromasil RP-18, 60 mm×2 mm, 3.5 µm; eluent A: 5 ml HClO$_4$/l water, eluent B: acetonitrile; gradient: 0 min 2% B, 0.5 min 2% B, 4.5 min 90% B, 6.5 min 90% B; flow rate: 0.75 ml/min; oven: 30° C.; UV-detektion: 210 nm.

Method B (HPLC): instrument: HP 1100 with DAD-detektion; column: Kromasil RP-18, 60 mm×2 mm, 3.5 µm; eluent A: 5 ml HClO$_4$/l water, eluent B: acetonitrile; gradient: 0 min 2% B, 0.5 min 2% B, 4.5 min 90% B, 9 min 90% B; flow rate: 0.75 ml/min; oven: 30° C.; UV-detektion: 210 nm.

Method C (preparative RP-HPLC): Column: GROM-SIL 120 ODS-4 HE 10 µm, 250 mm×30 mm; acetonitrile/water gradients.

Method D (LCMS): Instrument: Micromass Quattro LCZ with HPLC Agilent Serie 1100; column: Phenomenex Synergi 2µ Hydro-RP Mercury 20 mm×4 mm; eluent A: 1 l water+0.5 ml 50% formic acid, eluent B: 1 l acetonitrile+0.5 ml 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV-detektion: 208-400 nm.

Liquid Chromatography—Mass Spectroscopy (LC-MS): Micromass Platform LC with Shimadzu Phenomenex ODS column (30 mm×4.6 mm) flushing a mixture of acetonitrile-water (9:1 to 1:9) at 1 ml/min of the flow rate.

Mass Spectra

Electrospray (ES) ionization techniques (ESI): Perkin Elmer/SCIEX API 150MCA

Direct chemical ionization (DC): Finnigan MAT 95

Mass Determinations

Finnigan MAT MAT95

Melting points are uncorrected.

$^1$H NMR spectra were recorded using either Bruker DRX-300 (300 MHz for $^1$H) spectrometer, Brucker 500 UltraShielded™ (500 MHz for $^1$H), Bruker Avance 300 (300 MHz for $^1$H) or Bruker Avance 400 (400 MHz for $^1$H). Chemical shifts are reported in parts per million (ppm) with tetramethylsilane (TMS) as an internal standard at zero ppm. The abbreviations s, d, t, q, m, and br refer to singlet, doublet, triplet, quartet, multiplet, and broad, respectively.

All starting materials are commercially available or can be prepared using methods cited in the literature.

The effect of the present compounds was examined by the following assays and pharmacological tests.

[Measurement of Capsaicin-induced Ca$^{2+}$ influx in the Human VR1-transfected CHO Cell Line] (Assay 1)

(1) Establishment of the Human VR1-CHOluc9aeq Cell Line

Human vanilloid receptor (hVR1) cDNA was cloned from libraries of axotomized dorsal root ganglia (WO 00/29577). The cloned hVR1 cDNA was constructed with pcDNA3 vector and transfected into a CHOluc9aeq cell line. The cell line contains aequorin and CRE-luciferase reporter genes as read-out signals. The transfectants were cloned by limiting dilution in selection medium (DMEM/F12 medium (Gibco BRL) supplemented with 10% FCS, 1.4 mM Sodium pyruvate, 20 mM HEPES, 0.15% Sodium bicarbonate, 100 U/ml penicillin, 100 µg/ml streptomycin, 2 mM glutamine, non-essential amino acids and 2 mg/ml G418). Ca$^{2+}$ influx was examined in the capsaicin-stimulated clones. A high responder clone was selected and used for furter experiments in the project. The human VR1-CHOluc9aeq cells were maintained in the selection medium and passaged every 3-4 days at 1-2.5×10$^5$ cells/flask (75 mm$^2$).

(2) Measurement of Ca$^{2+}$ Influx Using FDSS-3000

Human VR1-CHOluc9aeq cells were suspended in a culture medium which is the same as the selection medium except for G418 and seeded at a density of 1,000 cells per well into 384-well plates (black walled clear-base/Nalge Nunc International). Following the culture for 48 hrs the medium was changed to 2 µM Fluo-3 AM (Molecular Probes) and 0.02% Puronic F-127 in assay buffer (Hank's balanced salt solution (HBSS), 17 mM HEPES (pH7.4), 1 mM Probenecid, 0.1% BSA) and the cells were incubated for 60 min at 25° C. After washing twice with assay buffer the cells were incubated with a test compound or vehicle for 20 min at 25° C. Mobilization of cytoplasmic Ca$^{2+}$ was measured by FDSS-3000 ($\lambda_{ex}$=488 nm, $\lambda_{em}$=540 nm/Hamamatsu Photonics) for 60 sec after the stimulation with 10 nM capsaicin. Integral R was calculated and compared with controls.

[Measurement of the Capsaicin-induced Ca$^{2+}$ Influx in Primary Cultured Rat Dorsal Root Ganglia Neurons] (Assay 2)

(1) Preparation of Rat Dorsal Root Ganglia Neurons

New born Wister rats (5-11 days) were sacrificed and dorsal root ganglia (DRG) was removed. DRG was incubated with 0.1% trypsin (Gibco BRL) in PBS(−) (Gibco BRL) for 30 min at 37° C., then a half volume of fetal calf serum (FCS) was added and the cells were spun down. The DRG neuron cells were resuspended in Ham F12/5% FCS/5% horse serum (Gibco BRL) and dispersed by repeated pipetting and passing through 70 µm mesh (Falcon). The culture plate was incubated for 3 hours at 37° C. to remove contaminating Schwann cells. Non-adherent cells were recovered and further cultured in laminin-coated 384 well plates (Nunc) at 1×10$^4$ cells/50 µl/well for 2 days in the presence of 50 ng/ml recombinant rat NGF (Sigma) and 50 µM 5-fluorodeoxyuridine (Sigma).

(2) Ca$^{2+}$ Mobilization Assay

DRG neuron cells were washed twice with HBSS supplemented with 17 mM BEPES (pH 7.4) and 0.1% BSA. After incubating with 2 µM fluo-3AM (Volectuar Probe), 0.02% PF127 (Gibco BRL) and 1 mM probenecid (Sigma) for 40 min at 37° C., cells were washed 3 times. The cells were incubated with VR1 antagonists or vehicle (dimethylsulfoxide) and then with 1 µM capsaicin in FDSS-6000 ($\lambda_{ex}$=480 mn, $\lambda_{em}$=520 nm/Hamamatsu Photonics). The fluorescence changes at 480 nm were monitored for 2.5 min. Integral R was calculated and compared with controls.

[Organ Bath Assay to Measure the Capsaicin-induced Bladder Contraction] (Assay 3)

Male Wistar rats (10 week old) were anesthetized with ether and sacrificed by dislocating the necks. The whole urinary bladder was excised and placed in oxygenated Modified Krebs-Henseleit solution (pH 7.4) of the following composition (112 mM NaCl, 5.9 mM KCl, 1.2 mM MgCl$_2$, 1.2 mM NaH$_2$PO$_4$, 2 mM CaCl$_2$, 2.5 mM NaHCO$_3$, 12 mM glucose). Contractile responses of the urinary bladder were studied as described previously

[Maggi C A et al: Br. J. Pharmacol. 108: 801-805, 1993]. Isometric tension was recorded under a load of 1 g using longitudinal strips of rat detrusor muscle. Bladder strips were equilibrated for 60 min before each stimulation. Contractile response to 80 mM KCl was determined at 15 min intervals until reproducible responses were obtained. The response to KCl was used as an internal standard to evaluate the maximal response to capsaicin. The effects of the compounds were investigated by incubating the strips with compounds for 30 min prior to the stimulation with 1 μM capsaicin (vehicle: 80% saline, 10% EtOH, and 10% Tween 80). One of the preparations made from the same animal was served as a control while the others were used for evaluating compounds. Ratio of each capsaicin-induced contraction to the internal standard (i.e. KCl-induced contraction) was calculated and the effects of the test compounds on the capsaicin-induced contraction were evaluated.

[Measurement of $Ca^{2+}$ Influx in the Human P2X1-transfected CHO Cell Line]
(1) Preparation of the Human P2X1-transfected CHOluc9aeq Cell Line
   Human P2X1-transfected CHOluc9aeq cell line was established and maintained in Dulbecco's modified Eagle's medium (DMEM/F12) supplemented with 7.5% FCS, 20 mM HEPES-KOH (pH 7.4),1.4 mM sodium pyruvate, 100 U/ml penicillin, 100 μg/ml streptomycin, 2 mM glutamine (Gibco BRL) and 0.5 Units/ml apyrase (grade I, Sigma). The suspended cells were seeded in each well of 384-well optical bottom black plates (Nalge Nunc International) at $3 \times 10^3/50$ μl /well. The cells were cultured for following 48 hrs to adhere to the plates.
(2) Measurement of the Intracellar $Ca^{2+}$ Levels
   P2X1 receptor agonist-mediated increases in cytosolic $Ca^{2+}$ levels were measured using a fluorescent $Ca^{2+}$ chelating dye, Fluo-3 AM (Molecular Probes). The plate-attached cells were washed twice with washing buffer (HBSS, 17 nM HEPES-KOH (pH 7.4), 0.1% BSA and 0.5 units/ml apyrase), and incubated in 40 μl of loading buffer (1 μM Fluo-3 AM, 1 mM probenecid, 1 μM cyclosporin A, 0.01% pluronic (Molecular Probes) in washing buffer) for 1 hour in a dark place. The plates were washed twice with 40 μl washing buffer and 35 μl of washing buffer were added in each well with 5 μl of test compounds or 2',3'-o-(2,4,6-trinitrophenyl) adenosine 5'-triphpsphate (Molecular Probes) as a reference. After further incubation for 10 minutes in dark 200 nM α, β-methylene ATP agonist was added to initiate the $Ca^{2+}$ mobilization. Fluorescence intensity was measured by FDSS-6000 ($\lambda_{ex}$=410 nm, $\lambda_{em}$=510 nm/Hamamatsu Photonics) at 250 msec intervals. Integral ratios were calculated from the data and compared with that of a control.

[Measurement of Capsaicin-induced Bladder Contraction in Anesthetized Rats] (Assay 4)
(1) Animals
   Female Sprague-Dawley rats (200~250 g/Charles River Japan) were used.
(2) Catheter Implantation
   Rats were anesthetized by intraperitoneal administration of urethane (Sigma) at 1.2 g/kg. The abdomen was opened through a midline incision, and a polyethylene catheter (BECTON DICKINSON, PE50) was implanted into the bladder through the dome. In parallel, the inguinal region was incised, and a polyethylene catheter (Hibiki, size 5) filled with 2 IU/ml of heparin (Novo Heparin, Aventis Pharma) in saline (Otsuka) was inserted into a common iliac artery.
(3) Cystometric Investigation
   The bladder catheter was connected via T-tube to a pressure transducer (Viggo-Spectramed Pte Ltd, DT-XXAD) and a microinjection pump (TERUMO). Saline was infused at room temperature into the bladder at a rate of 2.4 ml/hr. Intravesical pressure was recorded continuously on a chart pen recorder (Yokogawa). At least three reproducible micturition cycles, corresponding to a 20-minute period, were recorded before a test compound administration and used as baseline values.
(4) Administration of Test Compounds and Stimulation of Bladder with Capsaicin
   The saline infusion was stopped before administrating compounds. A testing compound dissolved in the mixture of ethanol, Tween 80 (ICN Biomedicals Inc.) and saline (1:1:8, v/v/v) was administered intraarterially at 10 mg/kg. 2 min after the administration of the compound 10 μg of capsaicin (Nacalai Tesque) dissolved in ethanol was administered intraarterially.
(5) Analysis of Cystometry Parameters
   Relative increases in the capsaicin-induced intravesical pressure were analyzed from the cystometry data. The capsaicin-induced bladder pressures were compared with the maximum bladder pressure during micturition without the capsaicin stimulation. The testing compounds-mediated inhibition of the increased bladder pressures was evaluated using Student's t-test. A probability level less than 5% was accepted as significant difference.

[Measurement of Over Active Bladder in Anesthetized Cystitis Rats] (Assay 5)
(1) Animals
   Female Sprague-Dawley rats (180~250 g/Charles River Japan) were used. Cyclophosphamide (CYP) dissolved in saline was administered intraperitoneally at 150 mg/kg 48 hours before experiment.
(2) Catheter Implantation
   Rats were anesthetized by intraperitoneal administration of urethane (Sigma) at 1.25 g/kg. The abdomen was opened through a midline incision, and a polyethylene catheter (BECTON DICKINSON, PE50) was implanted into the bladder through the dome. In parallel, the inguinal region was incised, and a polyethylene catheter (BECTON DICKINSON, PE50) filled with saline (Otsuka) was inserted into a femoral vein. After the bladder was emptied, the rats were left for 1 hour for recovery from the operation.
(3) Cystometric Investigation
   The bladder catheter was connected via T-tube to a pressure transducer (Viggo-Spectramed Pte Ltd, DT-XXAD) and a microinjection pump (TERUMO). Saline was infused at room temperature into the bladder at a rate of 3.6 ml/hr for 20 min. Intravesical pressure was recorded continuously on a chart pen recorder (Yokogawa). At least three reproducible micturition cycles, corresponding to a 20-minute period, were recorded before a test compound administration.
(4) Administration of Test Compounds
   A testing compound dissolved in the mixture of ethanol, Tween 80 (ICN Biomedicals Inc.) and saline (1:1:8, v/v/v) was administered intravenously at 0.05 mg/kg, 0.5 mg/kg or 5 mg/kg. 3 min after the administration of the compound, saline (Nacalai Tesque) was infused at room temperature into the bladder at a rate of 3.6 ml/hr.

(5) Analysis of Cystometry Parameters

The cystometry parameters were analyzed as described previously [Lecci A et al: Eur. J. Pharmacol. 259: 129-135, 1994]. The micturition frequency calculated from micturition interval and the bladder capacity calculated from a volume of infused saline until the first micturition were analyzed from the cystometry data. The testing compounds-mediated inhibition of the frequency and the testing compounds-mediated increase of bladder capacity were evaluated using unpaired Student's t-test. A probability levels less than 5% was accepted as significant difference. Data were analyzed as the mean±SEM from 4-7 rats.

[Measurement of Acute Pain]

Acute pain is measured on a hot plate mainly in rats. Two variants of hot plate testing are used: In the classical variant animals are put on a hot surface (52 to 56° C.) and the latency time is measured until the animals show nociceptive behavior, such as stepping or foot licking. The other variant is an increasing temperature hot plate where the experimental animals are put on a surface of neutral temperature. Subsequently this surface is slowly but constantly heated until the animals begin to lick a hind paw. The temperature which is reached when hind paw licking begins is a measure for pain threshold.

Compounds are tested against a vehicle treated control group. Substance application is performed at different time points via different application routes (i.v., i.p., p.o., i.t, i.c.v., s.c., intradermal, transdermal) prior to pain testing.

[Measurement of Persistent Pain]

Persistent pain is measured with the formalin or capsaicin test, mainly in rats. A solution of 1 to 5% formalin or 10 to 100 µg capsaicin is injected into one hind paw of the experimental animal. After formalin or capsaicin application the animals show nociceptive reactions like flinching, licking and biting of the affected paw. The number of nociceptive reactions within a time frame of up to 90 minutes is a measure for intensity of pain.

Compounds are tested against a vehicle treated control group. Substance application is performed at different time points via different application routes (i.v., i.p., p.o., i.t., i.c.v., s.c., intradermal, transdermal) prior to formalin or capsaicin administration.

[Measurement of Neuropathic Pain]

Neuropathic pain is induced by different variants of unilateral sciatic nerve injury mainly in rats. The operation is performed under anesthesia. The first variant of sciatic nerve injury is produced by placing loosely constrictive ligatures around the common sciatic nerve (Bennett and Xie, Pain 33 (1988): 87-107). The second variant is the tight ligation of about the half of the diameter of the common sciatic nerve (Seltzer et al., Pain 43 (1990): 205-218). In the next variant, a group of models is used in which tight ligations or transections are made of either the L5 and L6 spinal nerves, or the L5 spinal nerve only (KIM S H; CHUNG J M, AN EXPERIMENTAL-MODEL FOR PERIPHERAL NEUROPATHY PRODUCED BY SEGMENTAL SPINAL NERVE LIGATION IN THE RA, PAIN 50 (3) (1992): 355-363). The fourth variant involves an axotomy of two of the three terminal branches of the sciatic nerve (tibial and common peroneal nerves) leaving the remaining sural nerve intact whereas the last variant comprises the axotomy of only the tibial branch leaving the sural and common nerves uninjured. Control animals are treated with a sham operation.

Postoperatively, the nerve injured animals develop a chronic mechanical allodynia, cold allodynia, as well as a thermal hyperalgesia. Mechanical allodynia is measured by means of a pressure transducer (electronic von Frey Anesthesiometer, IITC Inc.-Life Science Instruments, Woodland Hills, SA, USA; Electronic von Frey System, Somedic Sales AB, Hörby, Sweden). Thermal hyperalgesia is measured by means of a radiant heat source (Plantar Test, Ugo Basile, Comerio, Italy), or by means of a cold plate of 5 to 10° C. where the nocifensive reactions of the affected hind paw are counted as a measure of pain intensity. A further test for cold induced pain is the counting of nocifensive reactions, or duration of nocifensive responses after plantar administration of acetone to the affected hind limb. Chronic pain in general is assessed by registering the circadanian rhytms in activity (Surjo and Arndt, Universität zu Köln, Cologne, Germany), and by scoring differences in gait (foot print patterns; FOOTPRINTS program, Klapdor et al., 1997. A low cost method to analyse footprint patterns. J. Neurosci. Methods 75, 49-54).

Compounds are tested against sham operated and vehicle treated control groups. Substance application is performed at different time points via different application routes (i.v., i.p., p.o., i.t., i.c.v., s.c., intradermal, transdermal) prior to pain testing.

[Measurement of Inflammatory Pain]

Inflammatory pain is induced mainly in rats by injection of 0.75 mg carrageenan or complete Freund's adjuvant into one hind paw. The animals develop an edema with mechanical allodynia as well as thermal hyperalgesia. Mechanical allodynia is measured by means of a pressure transducer (electronic von Frey Anesthesiometer, IITC Inc.-Life Science Instruments, Woodland Hills, SA, USA). Thermal hyperalgesia is measured by means of a radiant heat source (Plantar Test, Ugo Basile, Comerio, Italy, Paw thermal stimulator, G. Ozaki, University of California, USA). For edema measurement two methods are being used. In the first method, the animals are sacrificed and the affected hindpaws sectioned and weighed. The second method comprises differences in paw volume by measuring water displacement in a plethysmometer (Ugo Basile, Comerio, Italy).

Compounds are tested against uninflamed as well as vehicle treated control groups. Substance application is performed at different time points via different application routes (i.v., i.p., p.o., i.t., i.e.v., s.c., intradermal, transdermal) prior to pain testing.

[Measurement of Diabetic Neuropathic Pain]

Rats treated with a single intraperitoneal injection of 50 to 80 mg/kg streptozotocin develop a profound hyperglycemia and mechanical allodynia within 1 to 3 weeks. Mechanical allodynia is measured by means of a pressure transducer (electronic von Frey Anesthesiometer, IITC Inc.-Life Science Instruments, Woodland Hills, SA, USA).

Compounds are tested against diabetic and non-diabetic vehicle treated control groups. Substance application is performed at different time points via different application routes (i.v., i.p., p.o., i.t., i.c.v., s.c., intradermal, transdermal) prior to pain testing.

Results in capsaicin-induced $Ca^{2+}$ influx assay in the human VR1-transfected CHO cell line (Assay 1) are shown in Examples and tables of the Examples below. For practical reasons, the compounds are grouped in four classes based on activity as follows:

$IC_{50}=A(<or=)0.1\ \mu M<B(<or=)0.5\ \mu M<C(<or=)1\ \mu M<D$

The compounds of the present invention also show excellent selectivity, and strong activity in other assays 2-5 and assays for pain described above.

Preparing Method of Starting Compounds

[Starting Compound 1S]

(7-Ethoxy-5,8-dihydronaphthalen-1-yl)amine

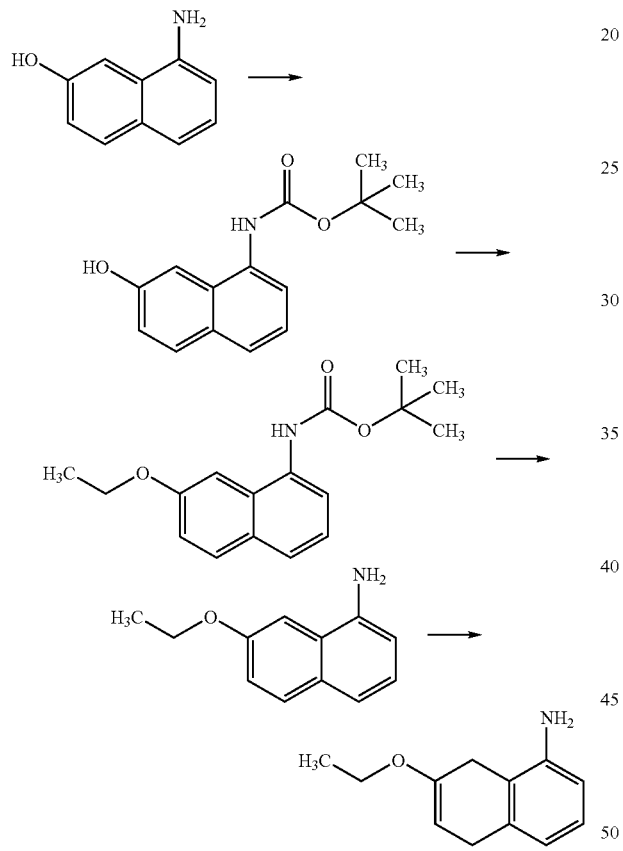

To a stirred solution of 8-amino-2-naphthol (50.0 g, 314 mmol) in tetrahydrofuran (1000 ml) was added di-t-butyldicarbonate (68.6 g, 314 mmol). The mixture was stirred at 70° C. for 18 hours. After the mixture was cooled to room temperature, solvent was removed under reduced pressure. To the residue was added ethylacetate, and washed with saturated aqueous solution of sodium carbonate and then with water. The extracted organic layer was dried over $Na_2SO_4$, filtered, and concentrated under reduced pressure. To the obtained residue was added diisopropyl ether, and the precipitate was filtered and dried to afford tert-butyl (7-hydroxy-1-naphthyl)carbamate (64.2 g, 79% yield).

Next, to a mixture of tert-butyl (7-hydroxy-1-naphthyl)carbamate (64.0 g, 247 mmol) and Cesium carbonate (161 g, 493 mmol) in 300 ml of anhydrous DMF was added iodoethane (42.3 g, 272 mmol) at room temperature. The mixture was stirred at 60° C. for 2 hours. Water was added to the mixture, and the product was extracted with ethyl acetate. The organic layer was washed with water and brine, dried over $Na_2SO_4$, filtered, and concentrated under reduced pressure. To the obtained residue was added diisopropyl ether and the precipitate was collected and dried to afford tert-butyl (7-ethoxy-1-naphthyl)carbamate (47.9 g, 67.5% yield).

Next, to a solution of tert-butyl (7-ethoxy-1-naphthyl)carbamate (47.9 g, 167 mmol) in 100 ml of anhydrous 1,4-dioxane was added 4N HCl in 1,4-dioxane (100 ml) at 0° C. The mixture was stirred at room temperature for 2 hours. Diisopropyl ether was added to the reaction mixture and the precipitate was filtered. To the obtained solid was added saturated sodium bicarbonate and the product was extracted with ethylacetate. The organic layer was dried over $Na_2SO_4$, filtered, and concentrated under reduced pressure to afford (7-ethoxy-1-naphthyl)amine (27.0 g, 86.3% yield).

Next, to a mixture of (7-ethoxy-1-naphthyl)amine (1.80 g, 9.61 mmol) and tert-butanol (2.13 g, 28.8 mmol) in tetrahydrofuran (20 mL) was collected liquid ammonia (300 mL) at −78° C. To the mixture was added lithium (0.200 g, 28.8 mmol) over 30 minutes and stirred at −78° C. for 1 hour. Methanol and water was added, and the mixture was stirred at room temperature for 16 hours to allow ammonia to evaporate. To the obtained residue was added ethyl acetate. The organic layer was washed with water, dried over $Na_2SO_4$, filtered, and concentrated under reduced pressure to afford (7-ethoxy-5,8-dihydronaphthalen-1-yl)amine (1.37 g, 76% yield).

[Starting Compound 2S]

8-amino-1,2,3,4-tetrahydro-naphthalen-2-ol

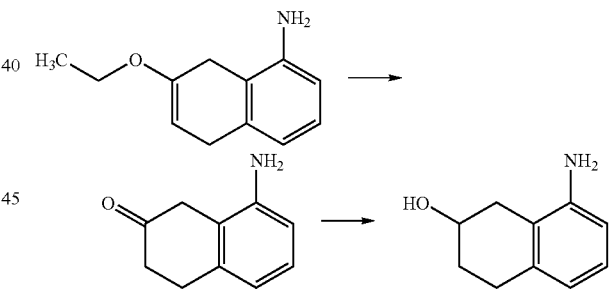

To a stirred solution of (7-ethoxy-5,8-dihydronaphthalen-1-yl)amine (1.07 g, 5.65 mmol) in tetrahydrofuran (30 ml) was added solution of aqueous 2N HCl (10 mL), and stirred at 40° C. for 1 hour. The mixture was neutralized with addition of sodium bicarbonate, and the product was extracted with ethyl acetate. The organic layer was washed with water, dried over $Na_2SO_4$, filtered, and concentrated under reduced pressure to afford 8-amino-3,4-dihydronaphthalen-2(1H)-one (0.71 g, 78% yield).

Next, to a solution of 8-amino-3,4-dihydronaphthalen-2(1H)-one (0.050 g, 0.318 mmol) in methanol (10 ml) was added sodium borohydride (0.030 g, 0.175 mmol) at 0° C., and the mixture was stirred for 1 hour. The mixture was poured into water, and the product was extracted with ethyl acetate. The organic layer was dried over $Na_2SO_4$, filtered, and concentrated under reduced pressure to afford 8-amino-1,2,3,4-tetrahydro-naphthalen-2-ol (0.037 g, 71% yield).

[Starting Compound 3S]

8-Amino-1,2,3,4-tetrahydro-naphthalen-2-ol (enantiomer)

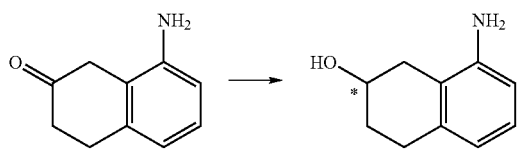

A stirred solution benzeneruthenium(II) chloride dimmer (1.55 g) and (1S, 2R)-(−)-cis-1-amino-2-indanol (1.85 g) in degassed isopropanol (500 ml) was heated at 80° C. for 20 minutes under argon, and then cooled to room temperature. The mixture was added to the solution of 8-amino-3,4-dihydro-1H-naphthalen-2-one (25.0 g) in isopropanol (700 ml) at room temperature followed by the prepared solution of potassium hydroxide (1.74 g) in 300 ml of isopropanol (pre-prepared at 45° C. to dissolve and then cooled to room temperature). After stirred at 45° C. for 30 minutes, the mixture was cooled to room temperature and was passed through silica gel pad and washed with ethylacetate. The filtrate was concentrated under reduced pressure, and the obtained solid was dissolved in dichloromethane and treated with activated charcoal for 10 minutes. After filtered through a silica gel pad, the mixture was concentrated under reduced pressure. The obtained product was recrystallized from dichloromethane to afford red crystal of (R)-8-amino-1,2,3,4-tetrahydro-naphthalen-2-ol (14 g, 56% yield).

The other enantiomer of 8-mino-1,2,3,4-tetrahydronaphthalen-2-ol was obtained in the same fashion replacing (1S, 2R)-(−)-cis-1-amino-2-indanol with (1R,2S)-(+)-cis-1-amino-2-indanol.

[Starting Compound 4S]

(3-Chlorophenyl)-piperidine-4-carboxylic acid

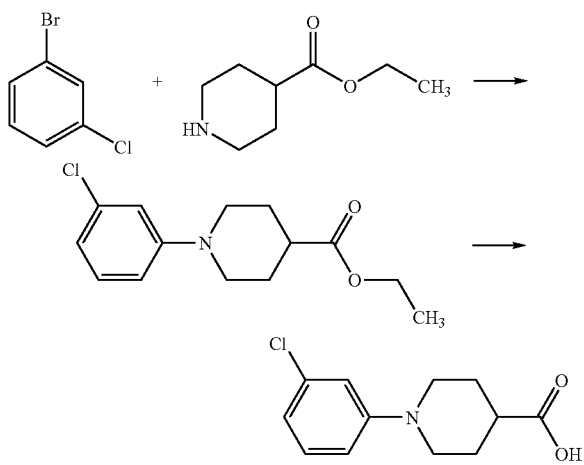

In a dried, screwcapped test tube under argon to a mixture of 240 mg (2.49 mmol) sodium tert.-butanolate, 33 mg (0.04 mmol) of tris-(dibenzylideneacetone)-dipalladium(0) and 42 mg (0.11 mmol) of 2-dicyclohexylphosphino-2'-(N,N-dimethylamino)biphenyl in 3.1 ml of toluene were added 308 mg (1.96 mmol) of ethyl piperidinelcarboxylate and 341 mg (1.78 mmol) of 3-chlorobromobenzene. The mixture was stirred with heating overnight at 80° C. After cooling, ethyl acetate was added, solid material was filtered off, the solvents were evaporated and the residue was purified by preparative RP-HPLC in a water/acetonitrile gradient to yield ethyl 1-(3-chlorophenyl)-piperidine-4-carboxylate.

$^1$H NMR (CDCl$_3$) δ 1.27 (t, 3H), 1.85 (dtd, 2H), 1.97-2.06 (m, 2H), 2.44 (tt, 1H), 2.81 (td, 2H), 3.63 (dt, 2H), 4.16 (q, 2H), 6.76-6.82 (m, 2H), 6.88 (t, 1H), 7.15 (t, 1H).
MS(DCI/NH$_3$): m/z=268 (M+H)$^+$
HPLC (method A): R$_t$=4.14 min 158 mg (0.59 mmol) of ethyl 1-(3-chlorophenyl)-piperidine-4-carboxylate were dissolved in 2.30 ml of methanol and 0.3 ml of water, and 99 mg (1.77 mmol) of powdered potassium hydroxide were added. The mixture was stirred at room temperature overnight After evaporation of the solvent, water was added and the mixture was acidified to pH 2-3 with 2N hydrochloric acid. The aqueous phase was extracted with ethyl acetate three times, the combined organic phases were washed with saturated sodium chloride solution, dried over magnesium sulfate, filtered and evaporated to give 127 mg (90% yield) of 1-(3-chlorophenyl)-piperidine-4-carboxylic acid.

$^1$H NMR (CDCl$_3$) δ 1.86 (dtd, 2H), 2.05-2.10 (m, 2H), 2.52 (tt, 1H), 2.84 (ddd, 2H), 3.64 (dt, 2H), 6.77-6.83 (m, 2H), 6.89 (t, 1H), 7.15 (t, 1H), 10.0-12.0 (very broad, 1H).
Molecular weight: 239.70
MS(DCI/NH$_3$): m/z=240 M+H)$^+$
HPLC (method A): R$_t$=3.33 min

[Starting Compound 5S]

1-[15-(Trifluoromethyl)pyridin-2-yl]piperidine-4-carboxylic acid

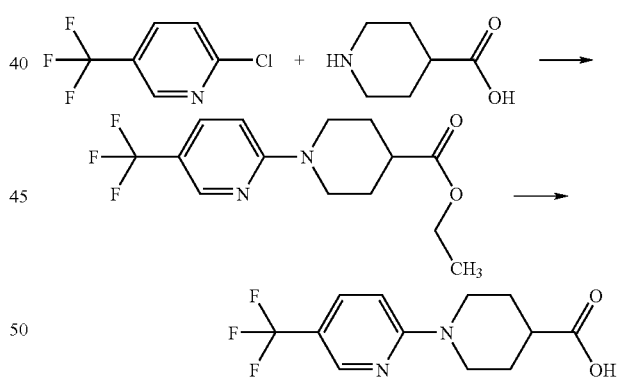

0.500 g (3.18 mmol) of ethyl piperidine-4-carboxylate, 0.866 g (4.77 mmol) of 2-chloro-5-trifluoromethylpyridine and 0.483 g (4.77 mmol) of triethylamine were reacted in dimethyl sulfoxide at 60° C. overnight. The reaction mixture was partitioned between ethyl acetate and water, the organic layer was washed with saturated sodium chloride, dried over magnesium sulfate, filtered and evaporated to dryness to yield crude ethyl 1-[5-(trifluoromethyl)pyridin-2-yl]piperidine-4-carboxylate.

The crude ethyl 1-[5-(trifluoromethyl)pyridin-2-yl]piperidine-4-carboxylate was dissolved in 15 ml of methanol and 2.5 ml of water. 535 mg (9.54 mmol) of potassium hydroxide were added and the mixture was reacted at 40° C. for 30 min. The mixture was evaporated, the residue was dissolved in water, pH 3 was adjusted with 2N hydrochloric acid and the solid formed was filtered off and dried in vacuo to yield 471 mg (54% yield) of 1-[5-trifluoromethyl)pyridin-2-yl]piperidine-4-carboxylic acid.

$^1$H NMR (DMSO-d$_6$) δ 1.42-1.60 (m, 2H), 1.81-1.93 (m, 2H), 2.50-2.62 (m, 1H), 3.00-3.14 (m, 2H), 4.21-4.36 (m, 2H), 6.95 (d, 1H), 7.75 (dd, 1H), 8.38 (d, 1H), 12.25 (s, 1H).

Molecular weight: 274.24
MS: m/z=275 (M+H)$^+$

In a similar manner as described in Starting compound 4S or 5S and by further modification of functional groups when needed, Starting compounds 6S to 23S as shown in Table A were synthesized.

TABLE A

| starting compound | structure | M.W. | MS property |
|---|---|---|---|
| 6S | 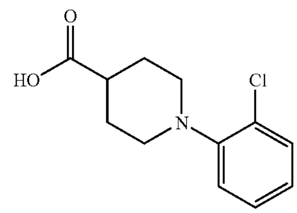 | 239.70 | 249 |
| 7S | 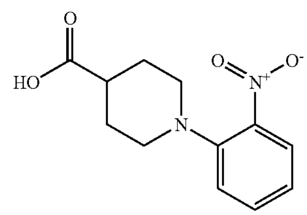 | 250.26 | 251 |
| 8S | 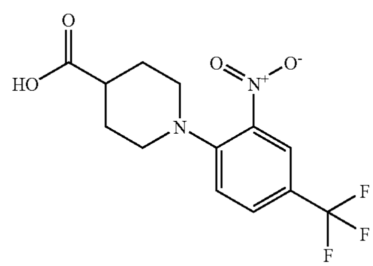 | 318.25 | 319 |
| 9S | 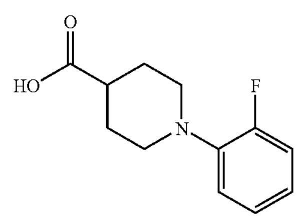 | 223.25 | 224 |
| 10S | 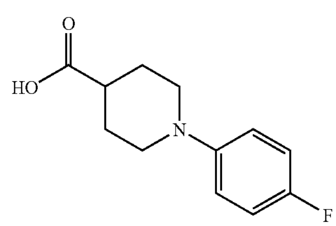 | 223.25 | 224 |
| 11S | 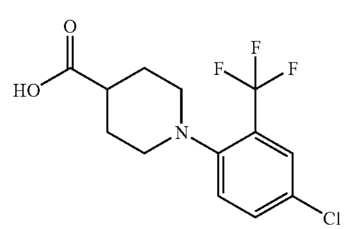 | 307.70 | 308 |

TABLE A-continued

| starting compound | structure | M.W. | MS | property |
|---|---|---|---|---|
| 12S | 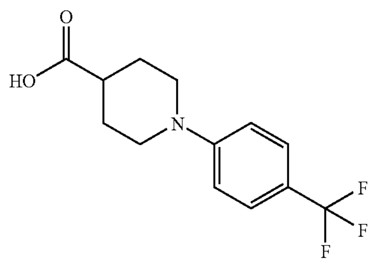 | 273.26 | 274 | |
| 13S | 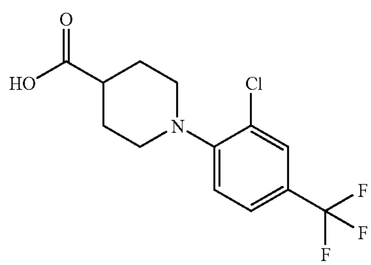 | 307.70 | 308 | HPLC (method A): $R_t$ = 4.79 min |
| 14S | 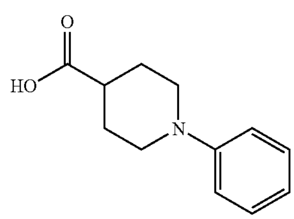 | 205.26 | 206 | HPLC (method A): $R_t$ = 2.79 min |
| 15S | 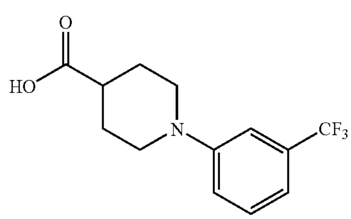 | 273.26 | 274 | HPLC (method A): $R_t$ = 3.68 min |
| 16S | 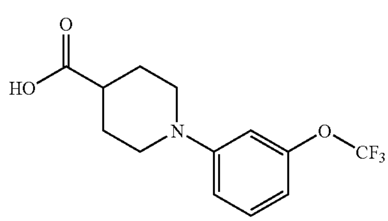 | 289.26 | 290 | HPLC (method A): $R_t$ = 3.82 min |
| 17S | 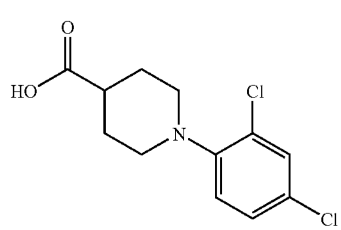 | 274.15 | 274 | HPLC (method A): $R_t$ = 4.62 min |

TABLE A-continued

| starting compound | structure | M.W. | MS | property |
|---|---|---|---|---|
| 18S | 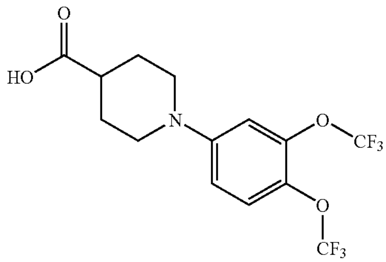 | 373.25 | 374 | HPLC (method A): R$_t$ = 4.76 min |
| 19S | 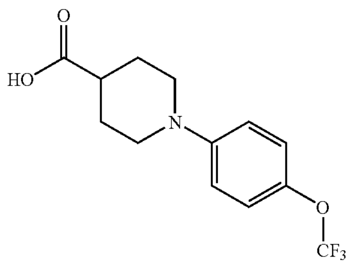 | 289.26 | 290 | HPLC (method A): R$_t$ = 3.71 min |
| 20S | 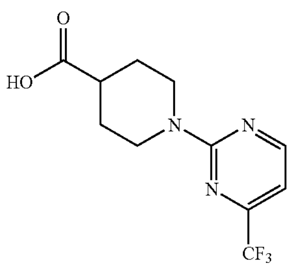 | 275.23 | 276 | HPLC (method A): R$_t$ = 4.34 min |
| 21S | 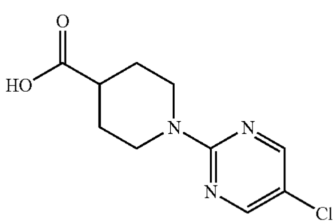 | 241.68 | 242 | HPLC (method A): R$_t$ = 3.98 min |
| 22S | 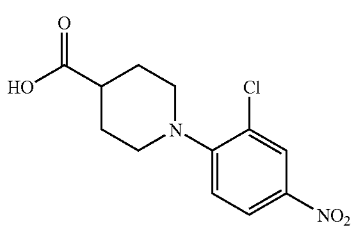 | 284.7 | 285 | HPLC (method A): R$_t$ = 4.39 min |
| 23S | 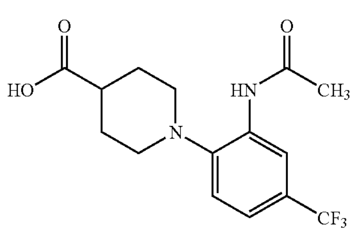 | 330.3 | 331 | |

[Starting compound 24S]

4-Amino-2,3-dihydro-1H-inden-2-yl acetate

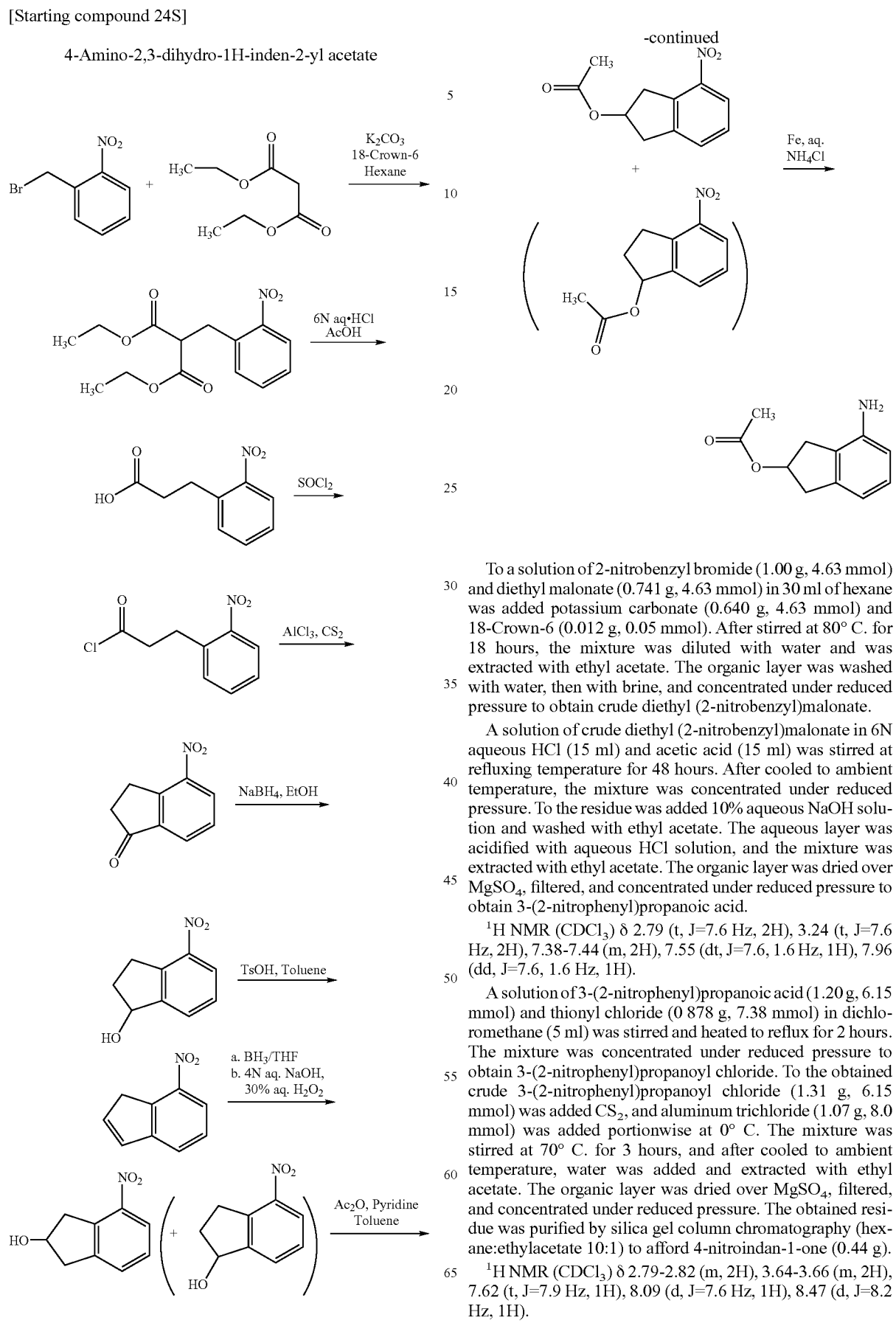

To a solution of 2-nitrobenzyl bromide (1.00 g, 4.63 mmol) and diethyl malonate (0.741 g, 4.63 mmol) in 30 ml of hexane was added potassium carbonate (0.640 g, 4.63 mmol) and 18-Crown-6 (0.012 g, 0.05 mmol). After stirred at 80° C. for 18 hours, the mixture was diluted with water and was extracted with ethyl acetate. The organic layer was washed with water, then with brine, and concentrated under reduced pressure to obtain crude diethyl (2-nitrobenzyl)malonate.

A solution of crude diethyl (2-nitrobenzyl)malonate in 6N aqueous HCl (15 ml) and acetic acid (15 ml) was stirred at refluxing temperature for 48 hours. After cooled to ambient temperature, the mixture was concentrated under reduced pressure. To the residue was added 10% aqueous NaOH solution and washed with ethyl acetate. The aqueous layer was acidified with aqueous HCl solution, and the mixture was extracted with ethyl acetate. The organic layer was dried over MgSO$_4$, filtered, and concentrated under reduced pressure to obtain 3-(2-nitrophenyl)propanoic acid.

$^1$H NMR (CDCl$_3$) δ 2.79 (t, J=7.6 Hz, 2H), 3.24 (t, J=7.6 Hz, 2H), 7.38-7.44 (m, 2H), 7.55 (dt, J=7.6, 1.6 Hz, 1H), 7.96 (dd, J=7.6, 1.6 Hz, 1H).

A solution of 3-(2-nitrophenyl)propanoic acid (1.20 g, 6.15 mmol) and thionyl chloride (0 878 g, 7.38 mmol) in dichloromethane (5 ml) was stirred and heated to reflux for 2 hours. The mixture was concentrated under reduced pressure to obtain 3-(2-nitrophenyl)propanoyl chloride. To the obtained crude 3-(2-nitrophenyl)propanoyl chloride (1.31 g, 6.15 mmol) was added CS$_2$, and aluminum trichloride (1.07 g, 8.0 mmol) was added portionwise at 0° C. The mixture was stirred at 70° C. for 3 hours, and after cooled to ambient temperature, water was added and extracted with ethyl acetate. The organic layer was dried over MgSO$_4$, filtered, and concentrated under reduced pressure. The obtained residue was purified by silica gel column chromatography (hexane:ethylacetate 10:1) to afford 4-nitroindan-1-one (0.44 g).

$^1$H NMR (CDCl$_3$) δ 2.79-2.82 (m, 2H), 3.64-3.66 (m, 2H), 7.62 (t, J=7.9 Hz, 1H), 8.09 (d, J=7.6 Hz, 1H), 8.47 (d, J=8.2 Hz, 1H).

To a solution of 4-nitroindan-1-one (0.381 g, 2.15 mmol) in ethanol (5 ml) was added sodium borohydride (0.048 g, 1.29 mmol) at 0° C., and the mixture was stirred at room temperature for 3 hours. Aqueous solution of ammonium chloride was added to the mixture, and extracted with ethyl acetate. The organic layer was dried over MgSO$_4$, filtered, and concentrated under reduced pressure to obtain 4-nitroindan-1-ol. $^1$H NMR (CDCl$_3$) δ 1.90 (d, J=6.5 Hz, 1H), 2.00-2.07 (m, 1H), 2.56-2.63 (m, 1H), 3.25-3.33 (m, 1H), 3.54-3.60 (m, 1H), 5.30-5.35 (m, 1H), 7.44 (t, J=8.2 Hz, 1H), 7.72 (d, J=7.6 Hz, 1H), 8.12 (d, J=8.2 Hz, 1H).

A solution of 4-nitroindan-1-ol (0.385 g, 2.15 mmol) and p-toluenesulfonic acid (5.0 mg, 0.03 mmol) in toluene (30 ml) was stirred and heated to reflux for 16 hours. After cooled to ambient temperature, the mixture was washed with aqueous sodium bicarbonate solution. The organic layer was dried over MgSO$_4$, filtered, and concentrated under reduced pressure. The obtained residue was purified by preparatory TLC (hexane:ethylacetate 3:1) to afford 7-nitro-1H-indene (0.289 g).

$^1$H NMR (CDCl$_3$) δ 3.94 (s, 2H), 6.75 (dt, J=5.7, 1.9 Hz, 1H), 6.93 (dt, J=5.7, 1.6 Hz, 1H), 7.45 (t, J=8.2 Hz, 1H), 7.68 (d, J=7.6 Hz, 1H), 8.05 (d, J=8.2 Hz, 1H).

To a solution of 2,3-dimethyl-2-butene (21.5 mg, 0.31 mmol) in THF (2 ml) at 0° C. was added borane-THF (0.307 ml, 0.31 mmol) dropwise. After stirred for 1 hour at 0° C., 7-nitro-1H-indene (45.0 mg, 0.28 mmol) in THF (5 ml) was added dropwise, and the mixture was stirred for 2 hours at ambient temperature. The mixture was cooled to 0° C., and water (0.15 ml), 4N aqueous sodium hydroxide (0.45 ml), and 30% H$_2$O$_2$ (0.45 ml) were added. The mixture was then warmed to room temperature and poured into water, extracted with ethyl acetate and washed with brine. The organic layer was dried over MgSO$_4$, filtered, and concentrated under reduced pressure. To the obtained mixture in toluene (1 ml) was added acetic anhydride (40.8 mg, 0.40 mmol) and pyridine (0.4 ml), and then stirred for 16 hours at room temperature. The mixture was concentrated under reduced pressure, and the obtained residue was purified by preparatory TLC (hexane:ethylacetate 2:1) to obtain 4-nitro-2,3-dihydro-1H-inden-2-yl acetate (16.0 mg).

$^1$H NMR (CDCl$_3$) δ 2.03 (s, 3H), 3.12 (dd, J=17.5, 1.6 Hz, 1H), 3.40 (dd, J=17.5, 6.3 Hz, 1H), 3.60 (dd, J=19.2, 2.2 Hz, 1H), 3.74 (dd, J=19.2, 6.6 Hz, 1H), 5.58-5.62 (m, 1H), 7.39 (t, J=7.9 Hz, 1H), 7.54 (d, J=7.3 Hz, 1H), 8.06 (d, J=8.2 Hz, 1H).

To a mixture of 4-nitro-2,3-dihydro-1H-inden-2-yl acetate (100 mg, 0.45 mmol) and ammonium chloride (100 mg) in ethanol (6 ml) and water (3 ml) was added iron powder (300 mg) portionwise at room temperature. The mixture was stirred at 90° C. for 1 hour, and after cooled to room temperature, the mixture was diluted with ethylacetate. The mixture was filtered through a pad of celite, and the filtrate was washed with brine, dried over MgSO$_4$, filtered, and concentrated under reduced pressure to obtain 4-amino-2,3-dihydro-1H-inden-2-yl acetate.

$^1$H NMR (CDCl$_3$) δ 2.03 (s, 3H), 2.81 (dd, J=16.4, 2.8 Hz, 1H), 3.00 (dd, J=16.7, 2.8 Hz, 1H), 3.14 (dd, J=16.4, 6.6 Hz, 1H), 3.29 (dd, J=16.7, 6.6 Hz, 1H), 3.58 (br.s, 2H), 5.51-5.56 (m, 1H), 6.54 (d, J=7.9 Hz, 1H), 6.69 (d, J=7.3 Hz, 1H), 7.04 (t, J=7.9 Hz, 1H).

Example 1-1

1-[2-Chloro-4-(trifluoromethyl)phenyl]-N-[(7S)-7-hydroxy-5,6,7,8-tetrahydro-naphthalen-1-yl]piperidine-4-carboxamide

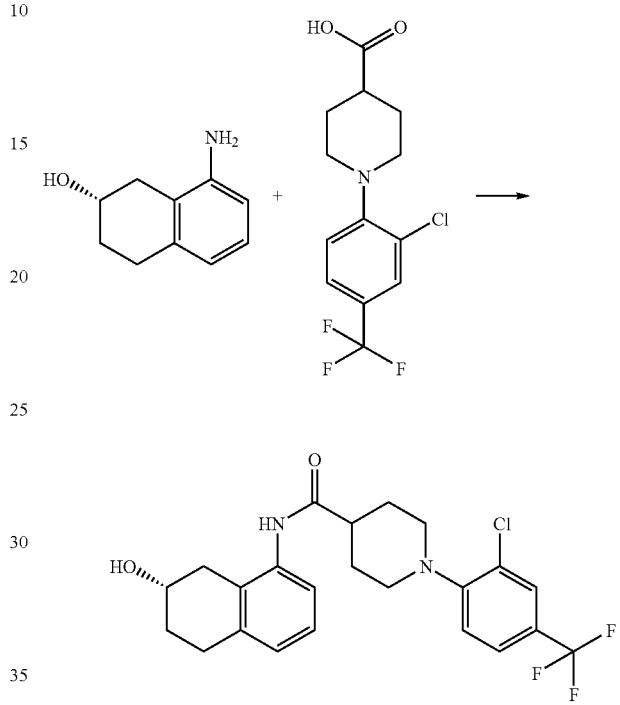

1-(2-Chlor-4-trifluoromethylphenyl)-piperidine-4-carboxylic acid (0.36 g, 1.16 mmol), (7S)-7-hydroxy-5,6,7,8-tetahydronaphthaleneamine (0.17 g, 1.05 mmol), 1-hydroxy-1H-benzotriazole (0.17 g, 126 mmol) and N-(3-dimethylaminopropyl)-N'-ethylcarbodiimide hydrochloride (0.26 g, 1.37 mmol) were combined in 10 ml of N,N-dimethylformamide under an argon atmosphere and stirred at room temperature overnight Water was added and the mixture was extracted with ethyl acetate three times. The combined organic phases were dried over magnesium sulfate, evaporated under reduced pressure, and the residue was separated over silica gel in ethyl acetate. Additional purification was achieved by preparative RP-HPLC using a water/acetonitrile gradient, yielding 1-[2-chloro-4-(trifluoromethyl)phenyl]-N-[(7S)-7-hydroxy-5,6,7,8-tetrahydro-naphthalen-1-yl]piperidine-4-carboxamide (0.132 g, 28% yield).

$^1$H NMR (DMSO-d$_6$) δ 1.53-1.65 (m, 1H), 1.80-2.00 (m, 5H), 2.43 (dd, 1H), 2.55-2.65 (m, 1H), 2.55-2.92 (m, 5H), 3.47 (d, 2H), 3.82-3.94 (m, 1H), 4.80 (d, 1H), 6.92 (d, 1H), 7.06 (t, 1H), 7.15 (d, 1H), 7.34 (d, 1H), 7.65 (d, 1H), 7.77 (s, 1H), 9.19 (s, 1H).

MS(ESIpos): m/z=453 (M+H)$^+$

HPLC (method B): R$_t$=4.72 min

Activity Class: A

Example 1-2

1-[3-Chlorophenyl]-N-[(7R)-7-hydroxy-5,6,7,8-tetrahydronaphthalen-1-yl]piperidine-4-carboxamide

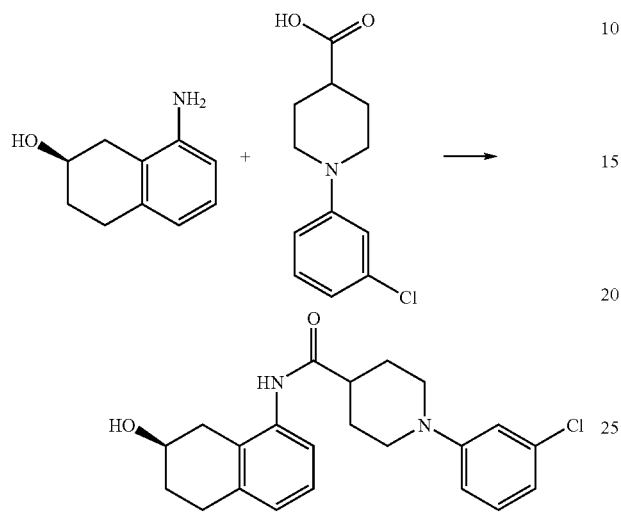

120 mg (0.50 mmol) of 1-(3-chlorophenyl)-piperidine-4-carboxylic acid, 74 mg (0.46 mmol) of (7R)-7-hydroxy-5,6,7,8-tetrahydronaphthaleneamine, 74 mg (0.55 mmol) of 1-hydroxy-1H-benzotriazole and 113 mg (0.59 mmol) of (N-(3-dimethylaminopropyl)-N'-ethylcarbodiimide hydrochloride were combined in 3 ml of N,N-dimethylformamide under an argon atmosphere and stirred at room temperature overnight. Ethyl acetate was added, the mixture washed with water and the aqueous phase re-extracted with ethyl acetate three times. The combined organic phases were dried over magnesium sulfate and evaporated under reduced pressure. The residue was purified by RP-BPLC in a water/acetonitrile gradient, yielding 57 mg (33% yield) of 1-[3-chlorophenyl]-N-[(7R)-7-hydroxy-5,6,7,8-tetrahydronaphthalen-1-yl]piperidine-4-carboxamide.

$^1$H NMR DMSO-$d_6$) δ 1.51-1.66 (m, 1H), 1.72 (qd, 2H), 1.80-1.94 (m, 3H), 2.42 (dd, 1H), 2.50-2.93 (m, 6H), 3.75-3.94 (m, 3H), 4.77 (d, 1H), 6.75 (dd, 1H), 6.87-6.98 (m, 3H), 7.05 (t, 1H), 7.14 (d, 1H), 7.20 (t, 1H), 9.13 (s, 1H).

MS(ESIpos): m/z=385 (M+H)$^+$

HPLC (method B): R$_t$=3.80 min

Activity Class: A

In a similar manner as described in Example 1-1 or 1-2, compounds in Example 1-3 to 1-25 as shown in Table 1 were synthesized.

TABLE 1

| exp # | structure | M.W. | MS | property | NMR | Activity Class |
|---|---|---|---|---|---|---|
| 1-3 | 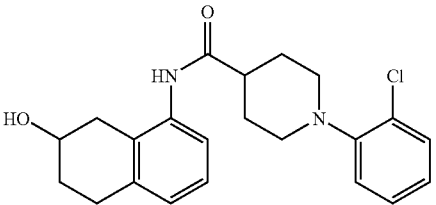 | 384.91 | 385 | mp: 210° C. | | A |
| 1-4 | 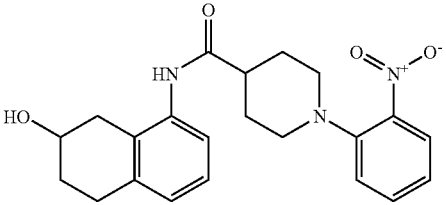 | 395.46 | 396 | mp: 170° C. | | A |
| 1-5 | 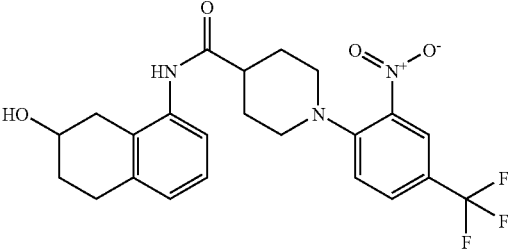 | 463.46 | 464 | mp: 218° C. | | A |

TABLE 1-continued

| exp # | structure | M.W. | MS | property | NMR | Activity Class |
|---|---|---|---|---|---|---|
| 1-6 | 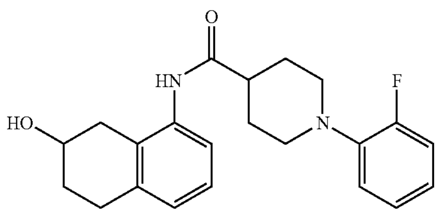 | 368.46 | 369 | mp: 207° C. | | A |
| 1-7 | 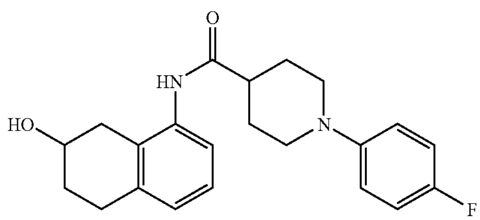 | 368.46 | 369 | mp: 205° C. | | A |
| 1-8 | 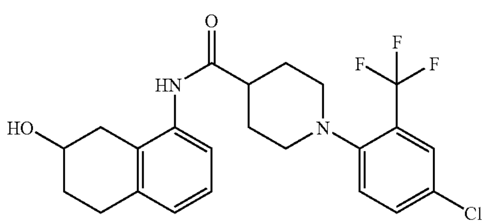 | 452.91 | 453 | mp: 182° C. | | A |
| 1-9 | 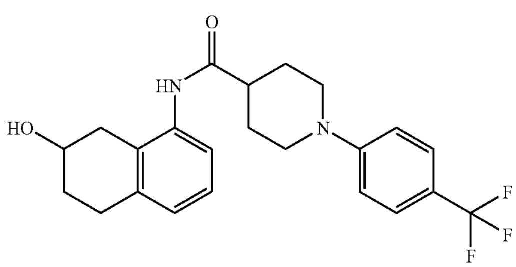 | 418.46 | 419 | mp: 222° C. | | A |
| 1-10 | 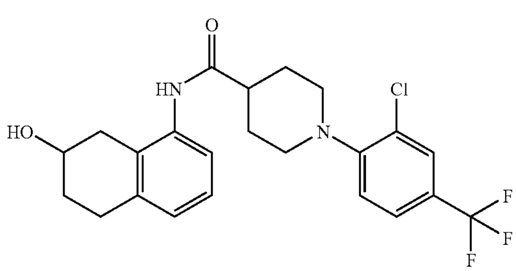 | 452.91 | 453 | mp: 226° C. | | A |
| 1-11 | Chiral | 368.46 | 369 | mp: 205° C. | | A |

TABLE 1-continued

| exp # | structure | M.W. | MS | property | NMR | Activity Class |
|---|---|---|---|---|---|---|
| 1-12 | 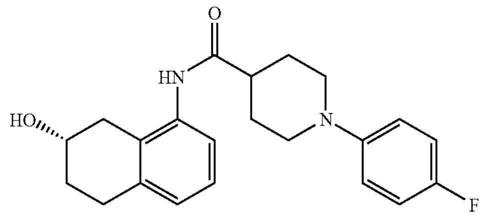 | 368.46 | 369 | mp: 205° C. | | A |
| 1-13 | 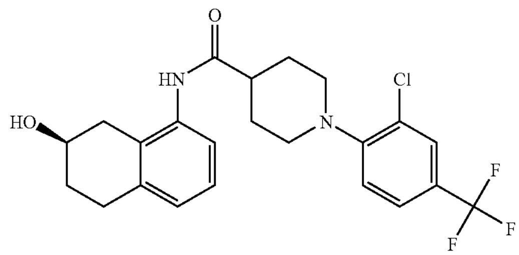 | 452.91 | 453 | mp: 226° C. | | A |
| 1-14 | 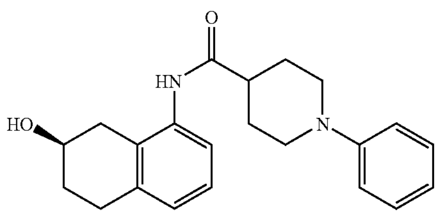 | 350.46 | 351 | HPLC (method A): R_t = 3.57 min | $^1$H NMR(DMSO-d$_6$) δ 1.51-1.66(m, 1H), 1.76 (qd, 2H), 1.82-1.95(m, 3H), 2.42 (dd, 1H), 2.50-2.65 (m, 1H), 2.65-2.80 (m, 3H), 2.80-2.93(m, 2H), 3.77(d, broad, 2H), 3.82-3.94(m, 1H), 4.77 (d, 1H), 6.76(t, 1H), 6.88-7.00 (m, 3H), 7.04(t, 1H), 7.11-7.25(m, 3H), 9.12 (s, 1H). | A |
| 1-15 | 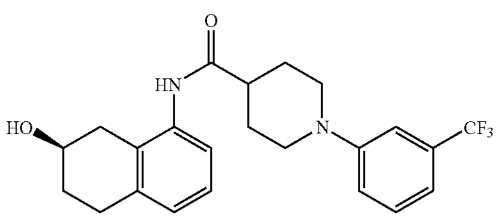 | 418.46 | 419 | HPLC (method A): R_t = 4.01 min | $^1$H NMR(DMSO-d$_6$) δ 1.50-1.67(m, 1H), 1.77-2.03 (m, 5H), 2.43(dd, 1H), 2.59-2.80(m, 2H), 2.80-2.96(m, 4H), 3.61 (d, 2H), 3.83-3.95(m, 1H), 4.77 (d, 1H), 6.92(d, 1H), 7.06(t, 1H), 7.15(d, 1H), 7.32(d, 1H), 8.15 (dd, 1H), 8.23(d, 1H), 9.18(s, 1H). | A |
| 1-16 | 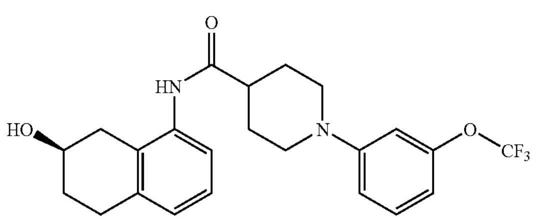 | 434.46 | 435 | HPLC (method B): R_t = 4.10 min | $^1$H NMR(DMSO-d$_6$) δ 1.51-1.66(m, 1H), 1.75 (qd, 2H), 1.81-1.96(m, 3H), 2.42(dd, 1H), 2.50-2.65 (m, 1H), 2.65-2.93 (m, 4H), 3.78(dt, broad, 2H), 3.82-3.94(m, 1H), 4.77(d, 1H), 6.91(d, 1H), 6.98-7.10(m, 3H), 7.16(t, 1H), 8.15(dd, 1H), 9.13 (s, 1H). | A |
| 1-17 | 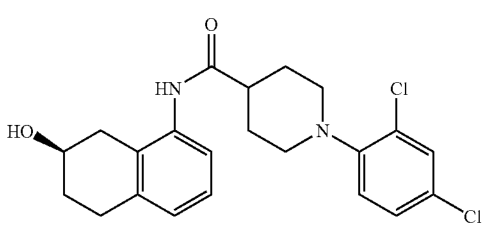 | 419.35 | 419 | HPLC (method B): R_t = 4.61 min | $^1$H NMR(DMSO-d$_6$) δ 1.51-1.67(m, 1H), 1.75-2.02 (m, 5H), 2.42(dd, 1H), 2.47-2.63(m, 1H), 2.63-2.79(m, 3H), 2.79-2.94 (m, 2H), 3.82-3.95 (m, 1H), 4.77(d, 1H), 6.92(d, 1H), 7.06(t, 1H), 7.15(d, 1H), 7.19(d, 1H), 7.36(dd, 1H), 7.53(d, 1H), 9.14(s, 1H). | A |

TABLE 1-continued

| exp # | structure | M.W. | MS | property | NMR | Activity Class |
|---|---|---|---|---|---|---|
| 1-18 | 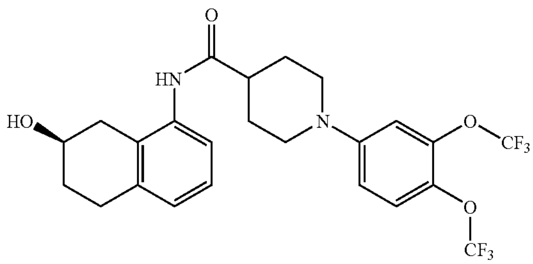 | 518.45 | 519 | HPLC (method A): R$_t$ = 4.87 min | $^1$H NMR(DMSO-d$_6$) δ 1.50-1.81(m, 3H), 1.81-1.97 (m, 3H), 2.42(dd, 1H), 2.55-2.95(m, 6H), 3.79-3.95(m, 3H), 4.77 (d, 1H), 6.91(d, 1H), 7.00-7.10(m, 3H), 7.14 (d, 1H), 7.39(d, 1H), 9.15 (s, 1H). | A |
| 1-19 | 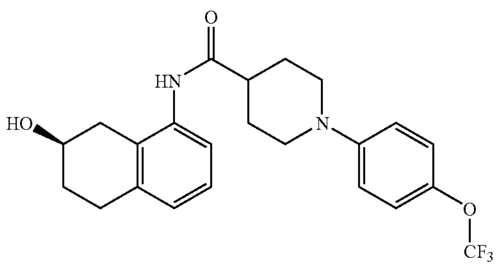 | 434.46 | 435 | HPLC (method A): R$_t$ = 3.94 min | $^1$H NMR(DMSO-d$_6$) δ 1.50-1.67(m, 1H), 1.75 (qd, 2H), 1.80-1.96(m, 3H), 2.42(dd, 1H), 2.50-2.93 (m, 6H), 3.78(d, 2H), 3.82-3.94(m, 1H), 4.77(d, 1H), 6.91(d, 1H), 6.98-7.10(m, 3H), 7.16(t, 3H), 9.13(s, 1H). | A |
| 1-20 | 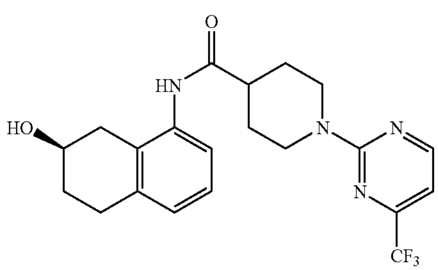 | 420.43 | 421 | HPLC (method A): R$_t$ = 4.38 min | $^1$H NMR(DMSO-d$_6$) δ 1.68(d, 1H), 1.73-1.92 (m, 3H), 1.98-2.13(m, 3H), 2.48-2.66(m, 2H), 2.78-3.12(m, 5H), 4.10-4.25 (m, 1H), 4.89(d, broad, 2H), 6.75(d, 1H), 6.90-7.00(m, 2H), 7.15(t, 1H), 7.58(d, broad, 1H), 8.49(d, 1H). | A |
| 1-21 | 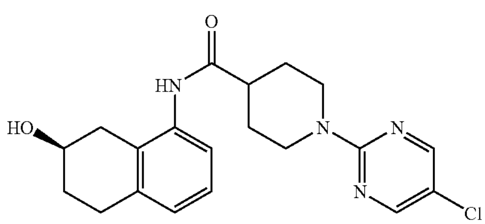 | 386.88 | 387 | HPLC (method A): R$_t$ = 4.11 min | $^1$H NMR(DMSO-d$_6$) δ 1.50-1.68(m, 1H), 1.80-1.96 (m, 1H), 2.41(dd, 1H), 2.64-2.92(m, 4H), 2.94-3.08(t, 2H), 3.81-3.95 (m, 1H), 4.63(d, broad, 2H) 4.76(d, 1H), 6.91(d, 1H), 7.04(t, 1H), 7.13(d, 1H), 8.41(s, 2H), 9.14(s, 1H). | A |
| 1-22 | 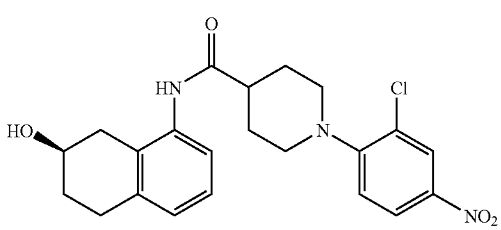 | 429.90 | 430 | HPLC (method B): R$_t$ = 4.47 min | $^1$H NMR(DMSO-d$_6$) δ 1.50-1.67(m, 1H), 1.77-2.03 (m, 5H), 2.43(dd, 1H), 2.59-2.80(m, 2H), 2.80-2.96(m, 4H), 3.61 (d, 2H), 3.83-3.95(m, 1H), 4.77(d, 1H), 6.92(d, 1H), 7.06(t, 1H), 7.15(d, 1H), 7.32(d, 1H), 8.15 (dd, 1H), 8.23(d, 1H), 9.18(s, 1H). | A |
| 1-23 | 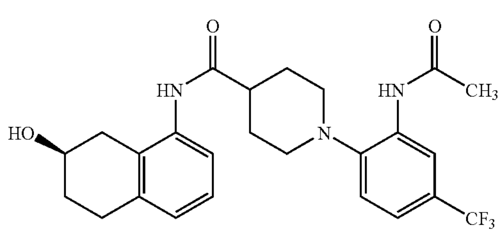 | 475.51 | 476 | HPLC (method A): R$_t$ = 4.17 min | $^1$H NMR(DMSO-d$_6$) δ 1.48-1.72(m, 1H), 1.80-2.25 (m, 8H, thereof 2.18 [s, 3H]), 2.34-2.95(m, 7H), 3.10-3.27(m, 2H), 3.80-3.98(m, 1H), 4.81 (d, 1H), 6.92(d, 1H), 7.05 (t, 1H), 7.17(d, 1H), 7.30 (d, 1H), 7.41(d, 1H), 8.17 (s, 1H), 9.08(s, 1H), 9.19 (s, 1H). | A |

TABLE 1-continued

| exp # | structure | M.W. | MS | property | NMR | Activity Class |
|---|---|---|---|---|---|---|
| 1-24 | 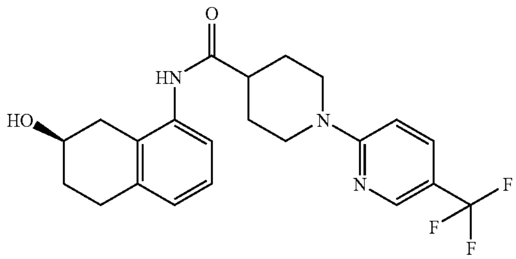 | 419.44 | 420 | HPLC (method A): $R_t$ = 3.68 min | $^1$H NMR(DMSO-d$_6$) δ 1.51-1.71(m, 3H), 1.80-2.00 (m, 3H), 2.41(dd, 1H), 2.64-2.92(m, 4H), 2.93-3.12(m, 2H), 3.81-3.93 (m, 1H), 4.40-4.52 (m, 2H), 4.75(d, 1H), 6.91(d, 1H), 6.98(d, 1H), 7.03(t, 1H), 7.12(d, 1H), 7.77(dd, 1H), 8.41(d, 1H), 9.15(s, 1H). | A |
| 1-25 | 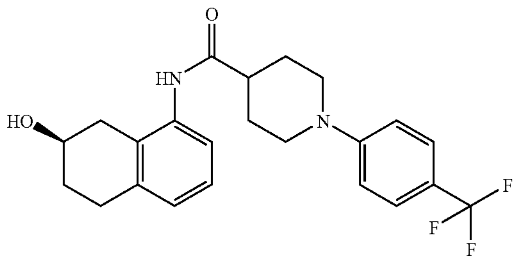 | 418.5 | 419 | HPLC (method A): $R_t$ = 4.16 min | $^1$H NMR(DMSO-d$_6$) δ 1.52-1.78(m, 3H), 1.81-1.97 (m, 3H), 2.41(dd, 1H), 2.60-2.78(m, 2H), 2.79-2.99(m, 4H), 3.81-4.01 (m, 3H), 4.81(d, 1H), 6.91(d, 1H), 7.01-7.18 (m, 4H), 7.50(d, 2H), 9.18(s, 1H). | A |

Example 2-1

A solution of (R)-8-amino-1,2,3,4-tetrahydro-naphthalen-2-ol (36.2 g) and pyridine (18.8 ml) in THF (850 ml) cooled at 0° C. was added phenyl chloroformate (28.8 ml). The mixture was stirred for 3 hours at room temperature, and then poured into ethylacetate. The mixture was washed with aqueous NH$_4$Cl then with water, and the organic layer was dried over Na$_2$SO$_4$, filtered, and concentrated under reduced pressure. To the obtained residue was added acetonitrile, and the precipitates were collected and washed with a mixture of acetonitrile and diisopropyl ether (2:3) to obtain phenyl [(R)-7-hydroxy-5,6,7,8-tetrahydronaphthalen-1-yl]carbamate (33.0 g).

MS(ES) m/z 284 [M+H]$^+$ $^1$H NMR (DMSO-d6) δ 1.59-1.64 (m, 1H), 1.83-1.89 (m, 1H), 2.68-2.99 (m, 4H), 3.90-3.92 (m, 1H), 4.84 (dd, J=3.8 Hz and 29.9 Hz, 1H), 6.75 (d, J=7.9 Hz, 1H), 7.07-7.25(m, 6H), 7.42 (t, J=7.85 Hz, 1H), 9.29(s, 1H).

Example 2-2

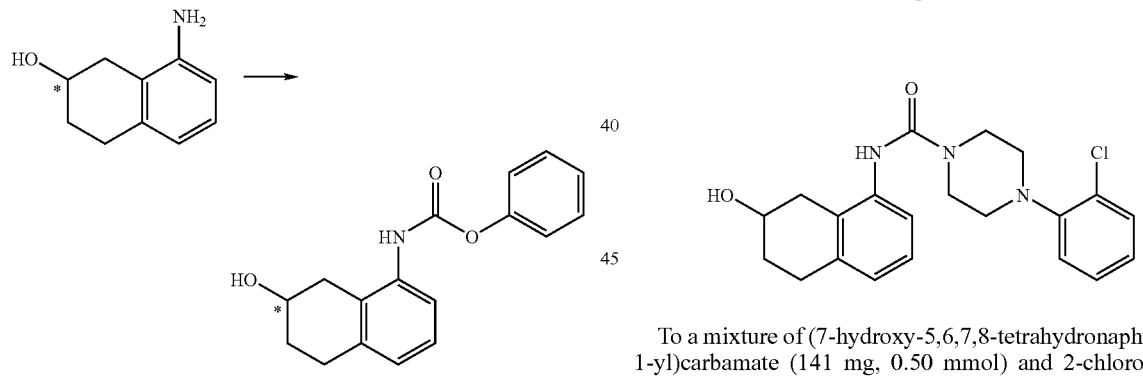

To a mixture of (7-hydroxy-5,6,7,8-tetrahydronaphthalen-1-yl)carbamate (141 mg, 0.50 mmol) and 2-chlorophenyl piperazine hydrochloride (155 mg, 0.66 mmol) in tetrahydrofuran (15 mL) was added 1,8-diazabicyclo[5.4.0]undec-7-ene (228 mg, 1.50 mmol) at room temperature, and the mixture was stirred for 30 minutes. Water was added and the mixture was extracted with ethylacetate. The organic layer was dried over Na2SO4, filtered, and concentrated under reduced pressure. The obtained residue was purified by silica gel column chromatography (eluent: ethylacetate/hexane=1/1) to provide 4-(2-chlorophenyl)-N-(7-hydroxy-5,6,7,8-tetrahydronaphthalen-1-yl)piperazine-1-carboxamide (103 mg).

MS (ESI) m/z 386 [M+H]$^+$ $^1$H NMR (MeOD-d$_6$) δ 1.68-1.75 (m, 1H), 2.01 (brs, 1H), 2.55 (dd, J=9.0, 12.9 Hz, 1H), 2.61-3.09 (m, 7H), 3.70 (m, 4H), 4.00 (brs, 1H), 6.99-7.09 (m, 4H), 7.17 (d, J=6.0 Hz, 1H), 7.26 (d, J=9.0 Hz, 1H), 7.39 (d, J=9.0 Hz, 1H).

Following compounds were prepared in a similar manner as described in Example 2-1:

Example 2-3

N-(7-hydroxy-5,6,7,8-tetydronaphthalen-1-yl)-4-[3-(trifluoromethyl)pyridin-2-yl]piperazine-1-carboxamide

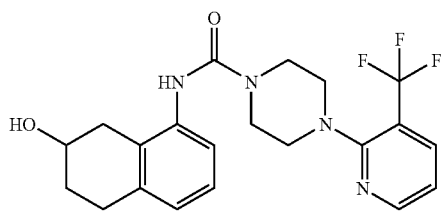

MS (ESI) m/z 421 [M+H]$^+$
$^1$H NMR MeOD-d6) δ 1.70-2.05 (m, 2H), 2.61 (dd, J=7.8, 12.9 Hz, 1H), 2.75-3.15 (m, 3H), 3.20-3.45 (m, 4H), 3.68 (brs, 4H), 4.01 (brs, 1H), 6.99-7.05 (m, 2H), 7.07 (d, J=9.0 Hz, 1H), 7.20 (dd, J=3.0, 9.0 Hz, 1H), 8.05 (d, J=9.0 Hz, 1H), 8.51 (d, J=3.0 Hz, 1H).

Example 2-4

4-cyclohexyl-N-7-hydroxy-5,6,7,8-tetrahydronaphthalen-1-yl)piperazine-1-carboxamide

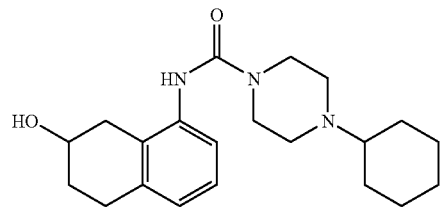

MS (ESI) m/z 358 [M+H]$^+$
$^1$H NMR (MeOD-d6) δ 1.20-1.51 (m, 5H), 1.70-2.15 (m, 7H), 2.31 (brs, 1H), 2.55 (dd, J=9.0, 12.9 Hz, 1H), 2.57-2.63 (m, 4H), 2.64-3.00 (m, 3H), 3.31-3.55 (m, 4H), 3.89 (brs, 1H), 6.967.07 (m, 3H).

Also, the following compounds are prepared in a similar manner.

TABLE 2

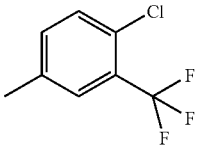

| Example | m | —X— | —R |
|---|---|---|---|
| 2-5 | 0 | bond | 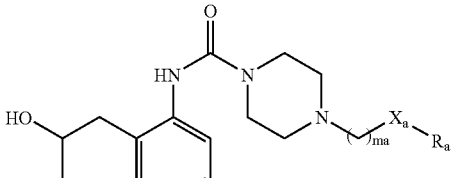 |

TABLE 2-continued

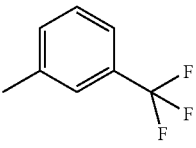

| Example | m | —X— | —R |
|---|---|---|---|
| 2-6 | 1 | bond | 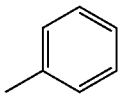 |
| 2-7 | 0 | bond | 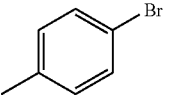 |
| 2-8 | 0 | —O— | 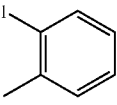 |
| 2-9 | 0 | —O— | 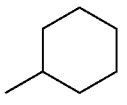 |
| 2-10 | 0 | —NH— | 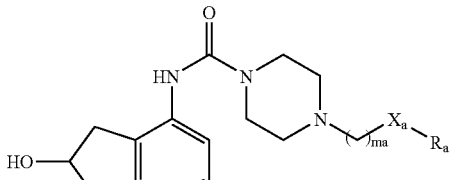 |
| 2-11 | 0 | —NH— | 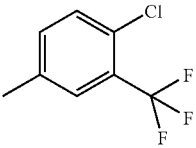 |

TABLE 3

| Example | m | —X— | —R |
|---|---|---|---|
| 3-1 | 0 | bond |  |

TABLE 3-continued

[Structure: indane with HO group, NH-C(O)-piperazine-N-(CH₂)ma-Xa-Ra]

| Example | m | —X— | —R |
|---------|---|-----|-----|
| 3-2 | 0 | bond | cyclohexyl |
| 3-3 | 0 | —O— | 4-chlorophenyl |
| 3-4 | 0 | —O— | 3-(ethoxycarbonyl)phenyl |
| 3-5 | 0 | —NH— | 3-methoxyphenyl |
| 3-6 | 1 | bond | 4-bromophenyl |
| 3-7 | 1 | bond | cyclohexyl |
| 3-8 | 1 | bond | 2-naphthyl |

TABLE 4

[Structure: tetrahydronaphthalene with HO group, NH-C(O)-piperazine-N-(CH₂)ma-Xa-Ra]

| Example | m | —X— | —R |
|---------|---|-----|-----|
| 4-1 | 1 | bond | 3-methyl-2-(trifluoromethyl)-6-piperidinophenyl |
| 4-2 | 0 | bond | cyclohexyl |
| 4-3 | 0 | —O— | 4-biphenylyl |
| 4-4 | 0 | —O— | 3-(ethoxycarbonyl)phenyl |
| 4-5 | 0 | —NH— | 3-methoxyphenyl |
| 4-6 | 1 | bond | 2-naphthyl |
| 3-7 | 1 | bond | cyclohexyl |

The invention claimed is:

1. A compound of the formula (I), their tautomeric and stereoisomeric form, and salts thereof:

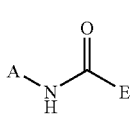
(I)

wherein
A represents the formula

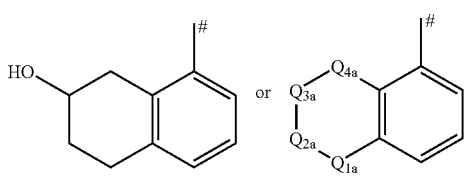

wherein
\# represents the connection position to the molecule,
$Q_{1a}$ and $Q_{4a}$ independently represent direct bond or methylene,
$Q_{2a}$ represents $CHR^{2a}$,
$Q_{3a}$ represents $CHR^{3a}$,
wherein
$R^{2a}$ represents group hydrogen, hydroxy, $C_{1-6}$ alkoxy or $C_{1-6}$ alkanoyloxy, and
$R^{3a}$ represents hydrogen, hydroxy, $C_{1-6}$ alkoxy, or $C_{1-6}$ alkanoyloxy, with the proviso that $Q_{1a}$ and $Q_{4a}$ can not be direct bond at the same time and $R^{2a}$ and $R^{3a}$ can not be hydrogen at the same time, and
E represents the formula

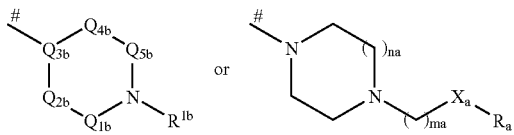

wherein
\# represents the connection position to the molecule,
$Q_{1b}$, $Q_{2b}$, $Q_{4b}$ and $Q_{5b}$ independently represent $C(R^{11b})(R^{12b})$,
wherein
$R^{11b}$ and $R^{12b}$ independently represent hydrogen, phenyl, benzyl, or $C_{1-6}$ alkyl optionally substituted by hydroxy, carboxy, phenyl, benzyl, $C_{1-6}$ alkoxy, $C_{1-6}$ alkoxycarbonyl, $C_{1-6}$ alkylamino, or di($C_{1-6}$ alkyl)amino;
$Q_{3b}$ represents $C—R^{13b}$,
wherein
$R^{13b}$ represents hydrogen, phenyl, benzyl, or $C_{1-6}$ alkyl optionally substituted by hydroxy, carboxy, phenyl, benzyl, $C_{1-6}$ alkoxy, $C_{1-6}$ alkoxycarbonyl, $C_{1-6}$ alkylamino, or di($C_{1-6}$ alkyl)amino;
$R^{1b}$ represents $C_{1-6}$ alkyl substituted by aryl or heteroaryl,
wherein
said aryl and heteroaryl are optionally substituted with one or more substituents selected from the group consisting of halogen, nitro, hydroxy, $C_{1-6}$ alkylamino, di($C_{1-6}$ alkyl)amino, $C_{3-8}$ cycloalkylamino, $C_{1-6}$ alkoxycarbonyl, phenyl, benzyl, heterocycle, sulfonamide, $C_{1-6}$ alkanoyl, $C_{1-6}$ alkanoylamino, carbamoyl, $C_{1-6}$ alkylcarbamoyl, cyano, $C_{1-6}$ alkyl optionally substituted by cyano, $C_{1-6}$ alkoxycarbonyl or mono-, di-, or tri-halogen, $C_{1-6}$ alkoxy optionally substituted by mono-, di-, or tri-halogen, phenoxy optionally substituted by halogen or $C_{1-6}$ alkyl, or $C_{1-6}$ alkylthio optionally substituted by mono-, di-, or tri-halogen, $C_{3-8}$ cycloalkyl, and heterocycle; or aryl or heteroaryl,
wherein
said aryl and heteroaryl are optionally substituted with one or more substituents selected from the group consisting of halogen, nitro, hydroxy, $C_{1-6}$ alkylamino, di($C_{1-6}$ alkyl)amino, $C_{3-8}$ cycloalkylamino, $C_{1-6}$ alkoxycarbonyl, phenyl, benzyl, heterocycle, sulfonamide, $C_{1-6}$ alkanoyl, $C_{1-6}$ alkanoylamino, carbamoyl, $C_{1-6}$ alkylcarbamoyl, cyano, $C_{1-6}$ alkyl optionally substituted by cyano, $C_{1-6}$ alkoxycarbonyl or mono-, di-, or tri-halogen, $C_{1-6}$ alkoxy optionally substituted by mono-, di-, or tri-halogen, phenoxy optionally substituted by halogen or $C_{1-6}$ alkyl, or $C_{1-6}$ alkylthio optionally substituted by mono-, di-, or tri-halogen, $C_{3-8}$ cycloalkyl, and heterocycle;

na represents 1 or 2;
ma represents 0, 1, 2, or 3;
—$X_a$— represents bond, —O— or —N($R^{1a}$)— (wherein $R^{1a}$ is hydrogen or $C_{1-6}$ alkyl); and
$R_a$ represents aryl or heteroaryl
wherein
said aryl and heteroaryl are optionally substituted with one or more substituents independently selected from the group consisting of halogen, nitro, hydroxy, carboxy, amino, $C_{1-6}$ alkylamino, di($C_{1-6}$ alkyl) amino, $C_{3-8}$ cycloalkylamino, $C_{1-6}$ alkoxycarbonyl, phenyl (which phenyl is optionally substituted by halogen, nitro, hydroxy, carboxy, amino, $C_{1-6}$ alkylamino, di($C_{1-6}$ alkyl)amino, $C_{3-8}$ cycloalkylamino, or $C_{1-6}$ alkoxycarbonyl), benzyl (in which phenyl moiety is optionally substituted by halogen, nitro, hydroxy, carboxy, amino, $C_{1-6}$ alkylamino, di($C_{1-6}$ alkyl) amino, $C_{3-8}$ cycloalkylamino, or $C_{1-6}$ alkoxycarbonyl), sulfonamide, $C_{1-6}$ alkanoyl, $C_{1-6}$ alkanoylamino, carbamoyl, $C_{1-6}$ alkylcarbamoyl, cyano, or a $C_{1-6}$ alkyl (which alkyl is optionally substituted by cyano, nitro, hydroxy, carboxy, amino, $C_{1-6}$ alkoxycarbonyl or mono-, di-, or tri-halogen), $C_{1-6}$ alkoxy (which alkoxy is optionally substituted by mono-, di-, or tri-halogen, phenoxy (in which phenyl moiety is optionally substituted by halogen, nitro, hydroxy, carboxy, amino, $C_{1-6}$ alkylamino, di($C_{1-6}$ alkyl)amino, $C_{3-5}$ cycloalkylamino, $C_{1-6}$ alkoxycarbonyl or $C_{1-6}$ alkyl), $C_{1-6}$ alkylthio optionally substituted by mono-, di-, or tri-halogen), $C_{3-8}$ cycloalkyl, and heterocycle.

2. Compound of formula (I) according to claim 1, with the formula (Ib), their tautomeric and stereoisomeric form, and salts thereof:

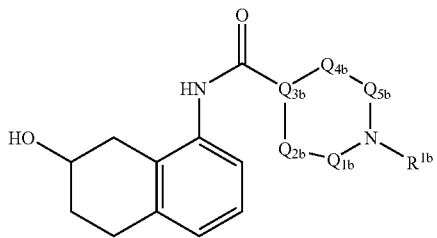

wherein $Q_{1b}$, $Q_{2b}$, $Q_{3b}$, $Q_{4b}$, $Q_{5b}$ and $R^{1b}$ are the same as defined in claim 1.

3. Compound of formula (I) according to claim 1, with the formula (Ia), their tautomeric and stereoisomeric form, and salts thereof:

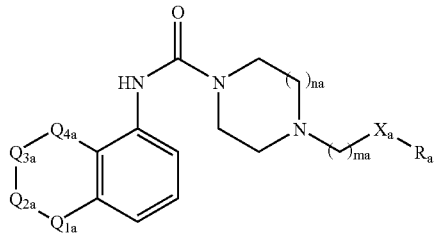

wherein $Q_{1a}$, $Q_{2a}$, $Q_{3a}$, $Q_{4a}$, na, ma, $X_a$ and $R_a$ are the same as defined in claim 1.

4. A process for synthesizing the compounds of general formula (I), wherein formula (I) contains the compounds of formula (Ib) and (Ia), according to claim 1, characterized in that

[Method Ab]

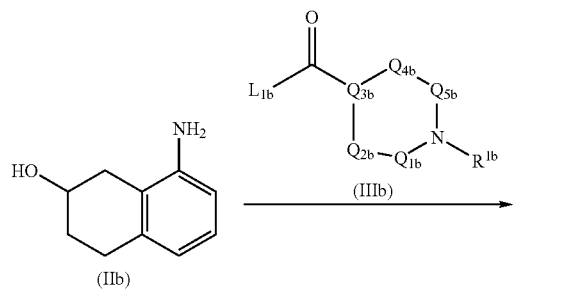

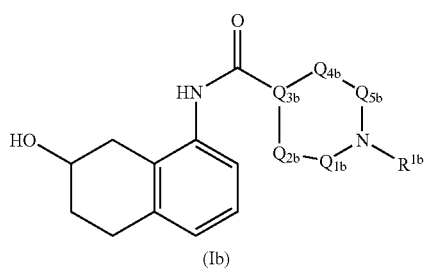

a compound of the formula (Ib), wherein $Q_{1b}$, $Q_{2b}$, $Q_{3b}$, $Q_{4b}$, $Q_{5b}$ and $R^{1b}$ are the same as defined in claim 1, can be prepared by the reaction of the compound of the formula (IIb) with the compound of the formula (IIIb), wherein $Q_{1b}$, $Q_{2b}$, $Q_{3b}$, $Q_{4b}$, $Q_{5b}$ and $R^{1b}$ are the same as defined in claim 1 and $L_{1b}$ represents a leaving group or

[Method Aa]

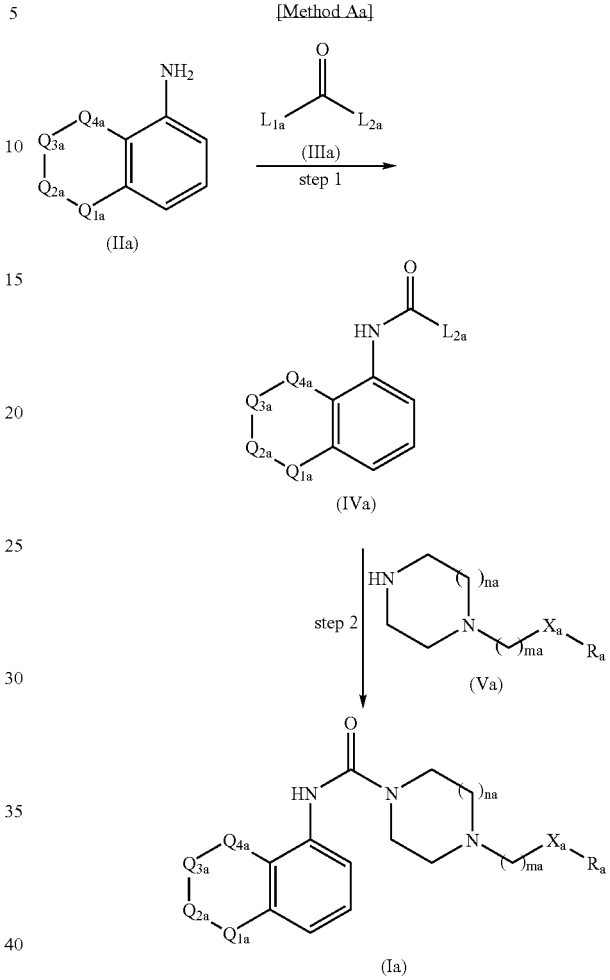

a compound of the formula (IVa), wherein $Q_{1a}$, $Q_{2a}$, $Q_{3a}$, and $Q_{4a}$, are the same as defined in claim 1, can be prepared by the reaction of the compound of the formula (IIa), wherein $Q_{1a}$, $Q_{2a}$, $Q_{3a}$, and $Q_{4a}$, are the same as defined in claim 1, with the compound of the formula (IIIa), wherein $L_{1a}$ represents a leaving group and $L_{2a}$ represents a leaving group and then the compound of the formula (Va), wherein na, ma, $X_a$ and $R_a$ are the same as defined in claim 1, is reacted with the compound (IVa) to obtain the compound of the formula (Ia), wherein $Q_{1a}$, $Q_{2a}$, $Q_{3a}$, $Q_{4a}$, na, ma, $X_a$ and $R_a$ are the same as defined in claim 1, or

[Method Ba]

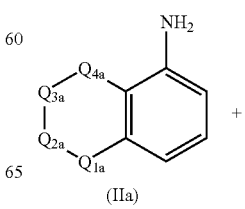

-continued

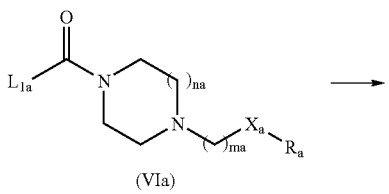

(VIa)

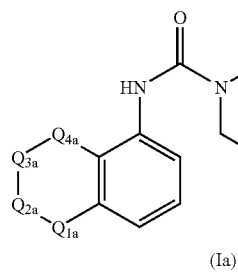

(Ia)

a compound of the formula (Ia) can be prepared by the reaction of the compound of the formula (IIa) and the compound of the formula (VIa), wherein na, ma, $X_a$, and $R_a$ are the same as defined in claim 1, and $L_{1a}$ is a leaving group as defined above, or

[Method Ca]

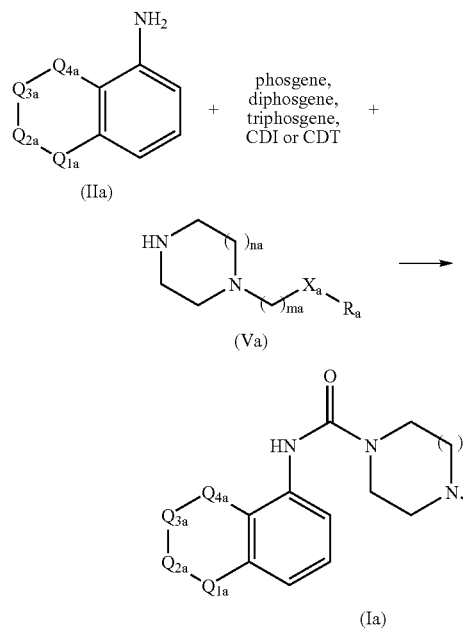

a compound of the formula (Ia) can be prepared by reacting the compound of the formula (IIa) with phosgene, diphosgene, triphosgene, 1,1-carbonyldiimidazole (CDI), or 1,1'-carbonyldi(1,2,4-triazole)(CDT), and then adding the compound of the formula (Va) to the reaction mixture, or

[Method Da]

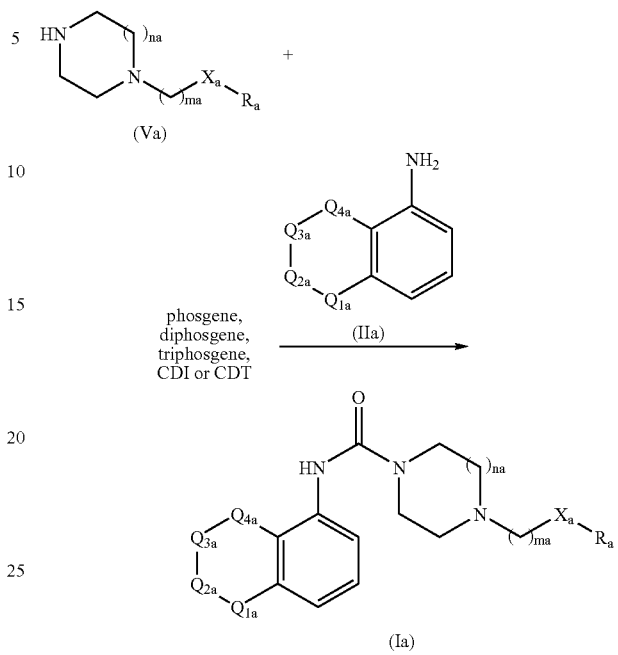

a compound of the formula (Ia) can be prepared by reacting the compound of the formula (Va) with phosgene, diphosgene, triphosgene, 1,1-carbonyldiimidazole (CDI), or 1,1'-carbonyldi(1,2,4-triazole)(CDT) and then adding the compound of the formula (IIa) to the reaction mixture.

5. A medicament comprising the compound of the formula (I), its tautomeric or stereoisomeric form, or a physiologically acceptable salt thereof as claimed in claim 1 as an active ingredient.

6. The medicament as claimed in claim 5, further comprising one or more pharmaceutically acceptable excipients.

7. The medicament as claimed in claim 5, wherein said compound of the formula (I), its tautomeric or stereoisomeric form, or a physiologically acceptable salt thereof is a VR1 antagonist.

8. A method for treating a urological disorder or disease in a human or animal, comprising administering to the human or animal a VR1-antagonistically effective amount of at least one compound according to claim 1, wherein the urological disorder or disease is selected from the group consisting of detrusor overactivity (overactive bladder), urinary incontinence, neurogenic detrusor overactivity (detrusor hyperflexia), idiopathic detrusor overactivity (detrusor instability), and benign prostatic hyperplasia.

9. A method for treating a disorder or disease related to pain in a human or animal, comprising administering to the human or animal a VR1-antagonistically effective amount of at least one compound according to claim 1, wherein the disorder or disease related to pain is selected from the group consisting of neuralgia, neuropathies, algesia, nerve injury, ischaemia, neurodegeneration, stroke, arthritis, cancer, irritable bowel syndrome and inflammatory lesions of joints, skin, muscles and nerves.

10. A method for treating an inflammatory disorder or disease in a human or animal, comprising administering to the human or animal a VR1-antagonistically effective amount of at least one compound according to claim 1, wherein the inflammatory disorder or disease is selected from the group consisting of asthma and COPD.

11. The compound of claim 1, wherein the compound is selected from the group consisting of: 1-(2-Chlorophenyl)-N-(7-hydroxy-5,6,7,8-tetrahydronaphthalen-1-yl)piperidine-4-carboxamide; N-(7-Hydroxy-5,6,7, 8-tetrahydronaphthalen-1-yl)-1-(2-nitrophenyl)piperidine-4-carboxamide; N-(7-Hydroxy-5,6,7,8-tetrahydronaphthalen-1-yl)-1-[2-nitro-4-(trifluoromethyl)phenyl]piperidine-4-carboxamide; 1-(2-Fluorophenyl)-N-(7-hydroxy-5,6,7,8-tetrahydronaphthalen-1-yl)piperidine-4-carboxamide; 1-(4-Fluorophenyl)-N-(7-hydroxy-5,6,7,8-tetrahydronaphthalen-1-yl)piperidine-4-carboxamide; 1-[4-Chloro-2-(trifluoromethyl)phenyl]-N-(7-hydroxy-5,6,7,8-tetrahydronaphthalen-1-yl)piperidine-4-carboxamide; N-(7-Hydroxy-5,6,7,8-tetrahydronaphthalen-1-yl)-1-[4-(trifluoromethyl)phenyl]piperidine-4-carboxamide; 1-[2-Chloro-4-(trifluoromethyl)phenyl]-N-(7-hydroxy-5,6,7,8-tetrahydronaphthalen-1-yl)piperidine-4-carboxamide; 1-(4-Fluorophenyl)-N-[(7R)-7-hydroxy-5,6,7,8-tetrahydronaphthalen-1-yl]piperidine-4-carboxamide; 1-[2-Chloro-4-(trifluoromethyl)phenyl]-N-[(7R)-7-hydroxy-5,6,7,8-tetrahydronaphthalen-1-yl]piperidine-4-carboxamide; 1-[2-Chloro-4-(trifluoromethyl)phenyl]-N-[(7S)-7-hydroxy-5,6,7,8-tetrahydro-naphthalen-1-yl]piperidine-4-carboxamide; 1-[3-Chlorophenyl]-N-[(7R)-7-hydroxy-5,6,7,8-tetrahydronaplithalen-1-yl]piperidine-4-carboxamide; N-[(7R)-7-Hydroxy-1-phenyl-5,6,7,8-tetrahydronaphthalen-1-yl]piperidine-4-carboxamide; N-[(7R)-7-Hydroxy-5,6,7,8-tetrahydronaphthalen-1-yl]-1-[3-trifluoromethyl-phenyl]piperidine-4-carboxamide; N-[(7R)-7Hydroxy-5,6,7,8-tetrahydronaphthalen-1-yl]-1-[3-trifluoromethoxy-phenyl]piperidine-4carboxamide; 1-[2,4-Dichlorophenyl]-N-[(7R)-7-hydroxy-5,6,7,8-tetrahydronaphthalen-1-yl]piperidine-4-carboxamide; 1-[3,4-Bis[trifluoromethoxy]phenyl]-N-[(7R)-7-hydroxy-5,6,7,8-tetrahydro-naphthalen-1-yl]piperidine-4-carboxamide; N-[(7R)-7-Hydroxy-5,6,7,8-tetrahydronaphthalen-1-yl]-1-[4-trifluoromethoxy-phenyl]piperidine-4-carboxamide; N-[(7R)-7-Hydroxy-5,6,7,8-tetrahydronaphthalen-1-yl]-1-[4-trifluoromethyl-pyrimidin-2-yl]piperidine-4-carboxamide; 1-[5-Chloropyrimidin-2-yl]-N-[(7R)-7-hydroxy-5,6,7,8-tetrahydronaphthalen-1-yl]piperidine-4-carboxamide; 1-[2-Chloro-4-nitrophenyl]-N-[(7R)-7-hydroxy-5,6,7,8-tetrahydronaphthalen-1-yl]piperidine-4-carboxamide; 1-[3-(Acetylamino)-5-(trifluoromethyl)pyridin-2-yl]-N-[(7R)-7-hydroxy-5,6,7,8-tetrahydronaphthalen-1-yl]piperidine-4-carboxamide; N-[(7R)-7-Hydroxy-5,6,7,8-tetrahydronaphthalen-1-yl]-1-[5-(trifluoromethyl)-pyridin-2-yl]piperidine-4-carboxamide; N-[(7R)-7-Hydroxy-5,6,7,8-tetrahydronaphthalen-1-yl]-1-[4-trifluoromethyl-phenyl]piperidine-4-carboxamide; and salts thereof.

12. The process of claim 4, wherein $L_{1b}$ is hydroxy, halogen, or azole.

13. The process of claim 12, wherein $L_{1b}$ is chlorine, bromine, or iodine.

14. The process of claim 12, wherein $L_{1b}$ is an imidazole or triazole.

15. The process of claim 4, wherein $L_{1a}$ is hydroxy, halogen or azole.

16. The process of claim 15, wherein $L_{1a}$ is a chlorine, bromine or iodine.

17. The process of claim 15, wherein $L_{1a}$ is imidazole or triazole.

18. The process of claim 4, wherein $L_{2a}$ is a halogen atom or a phenoxy group.

19. The process of claim 4, wherein $L_{2a}$ is a chlorine, bromine or iodine.

20. A method for treating pain in a human or animal, comprising administering to the human or animal a VR1-antagonistically effective amount of at least one compound according to claim 1, wherein said pain is selected from the group consisting of chronic pain, neuropathic pain, postoperative pain, rheumatoid arthritic pain, musculoskeletal pain, back pain, orofascial pain, headache, visceral pain, pelvic pain, vulvodynia, orchialgia and prostatodynia.

21. The method of claim 8, wherein the compound is selected from the group consisting of: 1-(2-Chlorophenyl)-N-(7-hydroxy-5,6,7,8-tetrahydronaphthalen-1-yl)piperidine-4-carboxamide; N-(7-Hydroxy-5,6,7,8-tetrahydronaphthalen-1-yl)-1-(2-nitrophenyl)piperidine-4-carboxamide; N-(7-Hydroxy-5,6,7,8-tetrahydronaphthalen-1-yl)-1-[2-nitro-4-(trifluoromethyl)phenyl]piperidine-4-carboxamide; 1-(2-Fluorophenyl)-N-(7-hydroxy-5,6,7,8-tetrahydronaphthalen-1-yl)piperidine-4-carboxamide; 1-(4-Fluorophenyl)-N-(7-hydroxy-5,6,7,8-tetrahydronaphthalen-1-yl)piperidine-4-carboxamide; 1-[4-Chloro-2-(trifluoromethyl)phenyl]-N-(7-hydroxy-5,6,7,8-tetrahydronaphthalen-1-yl)piperidine-4-carboxamide; N-(7-Hydroxy-5,6,7,8-tetrahydronaphthalen-1-yl)-1-[4-(trifluoromethyl)phenyl]piperidine-4-carboxamide; 1-[2-Chloro-4-(trifluoromethyl)phenyl]-N-(7-hydroxy-5,6,7,8-tetrahydronaphthalen-1-yl)piperidine-4-carboxamide; 1-(4-Fluorophenyl)-N-[(7R)-7-hydroxy-5,6,7,8-tetrahydronaphthalen-1-yl]piperidine-4-carboxamide; 1-[2-Chloro-4-(trifluoromethyl)phenyl]-N-[(7R)-7-hydroxy-5,6,7,8-tetrahydronaphthalen-1-yl]piperidine-4-carboxamide; 1-[2-Chloro-4-(trifluoromethyl)phenyl]-N-[(7S)-7-hydroxy-5,6,7,8-tetrahydro-naphthalen-1-yl]piperidine-4-carboxamide; 1-[3-Chlorophenyl]-N-[(7R)-7-hydroxy-5,6,7,8-tetrahydronaphthalen-1-yl]piperidine-4-carboxamide; N-[(7R)-7-Hydroxy-1-phenyl-5,6,7,8-tetrahydronaphthalen-1-yl]piperidine-4-carboxamide; N-[(7R)-7-Hydroxy-5,6,7,8-tetrahydronaphthalen-1-yl]-1-[3-trifluoromethyl-phenyl]piperidine-4-carboxamide; N-[(7R)-7-Hydroxy-5,6,7,8-tetrahydronaphthalen-1-yl]-1-[3-trifluoromethoxy-phenyl]piperidine-4-carboxamide; 1-[2,4-Dichlorophenyl]-N-[(7R)-7-hydroxy-5,6,7,8-tetrahydronaphthalen-1-yl]piperidine-4-carboxamide; 1-[3,4-Bis[trifluoromethoxy]phenyl]-N-[(7R)-7-hydroxy-5,6,7,8-tetrahydro-naphthalen-1-yl]piperidine-4-carboxamide; N-[(7R)-7-Hydroxy-5,6,7,8-tetrahydronaphthalen-1-yl]-1-[4-trifluoromethoxy-phenyl]piperidine-4-carboxamide; N-[(7R)-7-Hydroxy-5,6,7,8-tetrahydronaphthalen-1-yl]-1-[4-trifluoromethyl-pyrimidin-2-yl]piperidine-4-carboxamide; 1-[5-Chloropyrimidin-2-yl]-N-[(7R)-7-hydroxy-5,6,7,8-tetrahydronaphthalen-1-yl]piperidine-4-carboxamide; 1-[2-Chloro-4-nitrophenyl]-N-[(7R)-7-hydroxy-5,6,7,8-tetrahydronaphthalen-1-yl]piperidine-4-carboxamide; 1-[3-(Acetylamino)-5-(trifluoromethyl)pyridin-2-yl]-N-[(7R)-7-hydroxy-5,6,7,8-tetrahydronaphthalen-1-yl]piperidine-4-carboxamide; N-[(7R)-7-Hydroxy-5,6,7,8-tetrahydronaphthalen-1-yl]-1-[5-(trifluoromethyl)-pyridin-2-yl]piperidine-4-carboxamide; N-[(7R)-7-Hydroxy-5,6,7,8-tetrahydronaphthalen-1-yl]-1-[4-trifluoromethyl-phenyl]piperidine-4-carboxamide; and salts thereof.

22. The method of claim 9, wherein the compound is selected from the group consisting of: 1-(2-Chlorophenyl)-N-(7-hydroxy-5,6,7,8-tetrahydronaphthalen-1-yl)piperidine-4-carboxamide; N-(7-Hydroxy-5,6,7,8-tetrahydronaphthalen-1-yl)-1-(2-nitrophenyl)piperidine-4-carboxamide; N-(7-Hydroxy-5,6,7,8-tetrahydronaphthalen-1-yl)-1-[2-nitro-4-(trifluoromethyl)phenyl]piperidine-4- carboxamide; 1-(2-Fluorophenyl)-N-(7-hydroxy-5,6,7,8-tetrahydronaphthalen-1-yl)piperidine-4-carboxamide; 1-(4-Fluorophenyl)-N-(7-hydroxy-5,6,7,8-tetrahydronaphthalen-1-yl)piperidine-4-carboxamide; 1-[4-Chloro-2-(trifluoromethyl)phenyl]-N-(7-hydroxy-5,6,7,8-tetrahydronaphthalen-1-yl)piperidine-4-carboxamide; N-(7-Hydroxy-5,6,7,8-tetrahydronaphthalen-1-yl)-1-[4-(trifluoromethyl)phenyl]piperidine-4-carboxamide; 1-[2-Chloro-4-(trifluoromethyl)phenyl]-N-(7-hydroxy-5,6,7,8-tetrahydronaphthalen-1-yl)piperidine-4-carboxamide; 1-(4-Fluorophenyl)-N-[(7R)-7-hydroxy-5,6,7,8-tetrahydronaphthalen-1-yl]piperidine-4-carboxamide; 1-[2-Chloro-4-(trifluoromethyl)phenyl]-N-[(7R)-7-hydroxy-5,6,7,8-tetrahydronaphthalen-1-yl]piperidine-4-carboxamide; 1-[2-Chloro-4-(trifluoromethyl)phenyl]-N-[(7S)-7-hydroxy-5,6,7,8-tetrahydro-naphthalen-1-yl]piperidine-4-carboxamide; 1-[3-Chlorophenyl]-N-[(7R)-7-hydroxy-5,6,7,8-tetrahydronaphthalen-1-yl]piperidine-4-carboxamide; N-[(7R)-7-Hydroxy-1-phenyl-5,6,7,8-tetrahydronaphthalen-1-yl]piperidine-4-carboxamide; N-[(7R)-7-Hydroxy-5,6,7,8-tetrahydronaphthalen-1-yl]-1-[3-trifluoromethyl-phenyl]piperidine-4-carboxamide; N-[(7R)-7-Hydroxy-5,6,7,8-tetrahydronaphthalen-1-yl]-1-[3-trifluoromethoxy-phenyl]piperidine-4-carboxamide; 1-[2,4-Dichlorophenyl]-N-[(7R)-7-hydroxy-5,6,7,8-tetrahydronaphthalen-1-yl]piperidine-4-carboxamide; 1-[3,4-Bis[trifluoromethoxy]phenyl]-N-[(7R)-7-hydroxy-5,6,7,8-tetrahydro-naphthalen-1-yl]piperidine-4-carboxamide; N-[(7R)-7-Hydroxy-5,6,7,8-tetrahydronaphthalen-1-yl]-1-[4-trifluoromethoxy-phenyl]piperidine-4-carboxamide; N-[(7R)-7-Hydroxy-5,6,7,8-tetrahydronaphthalen-1-yl]-1-[4-trifluoromethyl-pyrimidin-2-yl]piperidine-4-carboxamide; 1-[5-Chloropyrimidin-2-yl]-N-[(7R)-7-hydroxy-5,6,7,8-tetrahydronaphthalen-1-yl]piperidine-4-carboxamide; 1-[2-Chloro-4-nitrophenyl]-N-[(7R)-7-hydroxy-5,6,7,8-tetrahydronaphthalen-1-yl]piperidine-4-carboxamide; 1-[3-(Acetylamino)-5-(trifluoromethyl)pyridin-2-yl]-N-[(7R)-7-hydroxy-5,6,7,8-tetrahydronaphthalen-1-yl]piperidine-4-carboxamide; N-[(7R)-7-Hydroxy-5,6,7,8-tetrahydronaphthalen-1-yl]-1-[5-(trifluoromethyl)-pyridin-2-yl]piperidine-4-carboxamide; N-[(7R)-7-Hydroxy-5,6,7,8-tetrahydronaphthalen-1-yl]-1-[4-trifluoromethyl-phenyl]piperidine-4-carboxamide; and salts thereof.

23. The method of claim 10, wherein the compound is selected from the group consisting of: 1-(2-Chlorophenyl)-N-(7-hydroxy-5,6,7,8-tetrahydronaphthalen-1-yl)piperidine-4-carboxamide; N-(7-Hydroxy-5,6,7,8-tetrahydronaphthalen-1-yl)-1-(2-nitrophenyl)piperidine-4-carboxamide; N-(7-Hydroxy-5,6,7,8-tetrahydronaphthalen-1-yl)-1-[2-nitro-4-(trifluoromethyl)phenyl]piperidine-4-carboxamide; 1-(2-Fluorophenyl)-N-(7-hydroxy-5,6,7,8-tetrahydronaphthalen-1-yl)piperidine-4-carboxamide; 1-(4-Fluorophenyl)-N-(7-hydroxy-5,6,7,8-tetrahydronaphthalen-1-yl)piperidine-4-carboxamide; 1-[4-Chloro-2-(trifluoromethyl)phenyl]-N-(7-hydroxy-5,6,7,8-tetrahydronaphthalen-1-yl)piperidine-4-carboxamide; N-(7-Hydroxy-5,6,7,8-tetrahydronaphthalen-1-yl)-1-[4-(trifluoromethyl)phenyl]piperidine-4-carboxamide; 1-[2-Chloro-4-(trifluoromethyl)phenyl]-N-(7-hydroxy-5,6,7,8-tetrahydronaphthalen-1-yl)piperidine-4-carboxamide; 1-(4-Fluorophenyl)-N-[(7R)-7-hydroxy-5,6,7,8-tetrahydronaphthalen-1-yl]piperidine-4-carboxamide; 1-[2-Chloro-4-(trifluoromethyl)phenyl]-N-[(7R)-7-hydroxy-5,6,7,8-tetrahydronaphthalen-1-yl]piperidine-4-carboxamide; 1-[2-Chloro-4-(trifluoromethyl)phenyl]-N-[(7S)-7-hydroxy-5,6,7,8-tetrahydro-naphthalen-1-yl]piperidine-4-carboxamide; 1-[3-Chlorophenyl]-N-[(7R)-7-hydroxy-5,6,7,8-tetrahydronaphthalen-1-yl]piperidine-4-carboxamide; N-[(7R)-7-Hydroxy-1-phenyl-5,6,7,8-tetrahydronaphthalen-1-yl]piperidine-4-carboxamide; N-[(7R)-7-Hydroxy-5,6,7,8-tetrahydronaphthalen-1-yl]-1-[3-trifluoromethyl-phenyl]piperidine-4-carboxamide; N-[(7R)-7-Hydroxy-5,6,7,8-tetrahydronaphthalen-1-yl]-1-[3-trifluoromethoxy-phenyl]piperidine-4-carboxamide; 1-[2,4-Dichlorophenyl]-N-[(7R)-7-hydroxy-5,6,7,8-tetrahydronaphthalen-1-yl]piperidine-4-carboxamide; 1-[3,4-Bis[trifluoromethoxy]phenyl]-N-[(7R)-7-hydroxy-5,6,7,8-tetrahydro-naphthalen-1-yl]piperidine-4-carboxamide; N-[(7R)-7-Hydroxy-5,6,7,8-tetrahydronaphthalen-1-yl]-1-[4-trifluoromethoxy-phenyl]piperidine-4-carboxamide; N-[(7R)-7-Hydroxy-5,6,7,8-tetrahydronaphthalen-1-yl]-1-[4-trifluoromethyl-pyrimidin-2-yl]piperidine-4-carboxamide; 1-[5-Chloropyrimidin-2-yl]-N-[(7R)-7-hydroxy-5,6,7,8-tetrahydronaphthalen-1-yl]piperidine-4-carboxamide; 1-[2-Chloro-4-nitrophenyl]-N-[(7R)-7-hydroxy-5,6,7,8-tetrahydronaphthalen-1-yl]piperidine-4-carboxamide; 1-[3-(Acetylamino)-5-(trifluoromethyl)pyridin-2-yl]-N-[(7R)-7-hydroxy-5,6,7,8-tetrahydronaphthalen-1-yl]piperidine-4-carboxamide; N-[(7R)-7-Hydroxy-5,6,7,8-tetrahydronaphthalen-1-yl]-1-[5-(trifluoromethyl)-pyridin-2-yl]piperidine-4-carboxamide; N-[(7R)-7-Hydroxy-5,6,7,8-tetrahydronaphthalen-1-yl]-1-[4-trifluoromethyl-phenyl]piperidine-4-carboxamide; and salts thereof.

24. The method of claim 20, wherein the compound is selected from the group consisting of: 1-(2-Chlorophenyl)-N-(7-hydroxy-5,6,7,8-tetrahydronaphthalen-1-yl)piperidine-4-carboxamide; N-(7-Hydroxy-5,6,7,8-tetrahydronaphthalen-1-yl)-1-(2-nitrophenyl)piperidine-4-carboxamide; N-(7-Hydroxy-5,6,7, 8-tetrahydronaphthalen-1-yl)-1-[2-nitro-4-(trifluoromethyl)phenyl]piperidine-4-carboxamide; 1-(2-Fluorophenyl)-N-(7-hydroxy-5,6,7,8-tetrahydronaphthalen-1-yl)piperidine-4-carboxamide; 1-(4-Fluorophenyl)-N-(7-hydroxy-5,6,7,8-tetrahydronaphthalen-1-yl)piperidine-4-carboxamide; 1-[4-Chloro-2-(trifluoromethyl)phenyl]-N-(7-hydroxy-5,6,7,8-tetrahydronaphthalen-1-yl)piperidine-4-carboxamide; N-(7-Hydroxy-5,6,7,8-tetrahydronaphthalen-1-yl)-1-[4-(trifluoromethyl)phenyl]piperidine-4-carboxamide; 1-[2-Chloro-4-(trifluoromethyl)phenyl]-N-(7-hydroxy-5,6,7,8-tetrahydronaphthalen-1-yl)piperidine-4-carboxamide; 1-(4-Fluorophenyl)-N-[(7R)-7-hydroxy-5,6,7,8-tetrahydronaphthalen-1-yl]piperidine-4-carboxamide; 1-[2-Chloro-4-(trifluoromethyl)phenyl]-N-[(7R)-7-hydroxy-5,6,7,8-tetrahydronaphthalen-1-yl]piperidine-4-carboxamide; 1-[2-Chloro-4-(trifluoromethyl)phenyl]-N-[(7S)-7-hydroxy-5,6,7,8-tetrahydro-naphthalen-1-yl]piperidine-4-carboxamide; 1-[3-Chlorophenyl]-N-[(7R)-7-hydroxy-5,6,7,8-tetrahydronaphthalen-1-yl]piperidine-4-carboxamide; N-[(7R)-7-Hydroxy-1-phenyl-5,6,7,8-tetrahydronaphthalen-1-yl]piperidine-4-carboxamide; N-[(7R)-7-Hydroxy-5,6,7,8-tetrahydronaphthalen-1-yl]-1-[3-trifluoromethyl-phenyl]piperidine-4-carboxamide; N-[(7R)-7-Hydroxy-5,6,7,8-tetrahydronaphthalen-1-yl]-1-[3-trifluoromethoxy-phenyl]piperidine-4-carboxamide; 1-[2,4-Dichlorophenyl]-N-[(7R)-7-hydroxy-5,6,7,8-tetrahydronaphthalen-1-yl]piperidine-4-carboxamide; 1-[3,4-Bis[trifluoromethoxy]phenyl]-N-[(7R)-7-hydroxy-5,6,7,8-tetrahydro-naphthalen-1-yl]piperidine-4-carboxamide; N-[(7R)-7-Hydroxy-5,6,7,8-tetrahydronaphthalen-1-yl]-1-[4-trifluoromethoxy-phenyl]piperidine-4-carboxamide; N-[(7R)-7-Hydroxy-5,6,7,8-tetrahydronaphthalen-1-yl]-1-[4-trifluoromethyl-pyrimidin-2-yl]piperidine-4-carboxamide; 1-[5-Chloropyrimidin-2-yl]-N-[(7R)-7-hydroxy-5,6,7,8-tetrahydronaphthalen-1-yl]piperidine-4-carboxamide; 1-[2-

Chloro-4-nitrophenyl]-N-[(7R)-7-hydroxy-5,6,7,8-tetrahydronaphthalen-1-yl]piperidine-4-carboxamide; 1-[3-(Acetylamino)-5-(trifluoromethyl)pyridin-2-yl]-N-[(7R)-7-hydroxy-5,6,7,8-tetrahydronaphthalen-1-yl]piperidine-4-carboxamide; N-[(7R)-7-Hydroxy-5,6,7,8-tetrahydronaphthalen-1-yl]-1-[5-(trifluoromethyl)-pyridin-2-yl]piperidine-4-carboxamide; N-[(7R)-7-Hydroxy-5,6,7,8-tetrahydronaphthalen-1-yl]-1-[4-trifluoromethyl-phenyl]piperidine-4-carboxamide; and salts thereof.

25. A method for treating lower urinary tract symptoms in a human or animal, comprising administering to the human or animal a VR1-antagonistically effective amount of at least one compound according to claim 1.

26. The method of claim 25, wherein the compound is selected from the group consisting of: 1-(2-Chlorophenyl)-N-(7-hydroxy-5,6,7,8-tetrahydronaphthalen-1-yl)piperidine-4-carboxamide; N-(7-Hydroxy-5,6,7,8-tetrahydronaphthalen-1-yl)-1-(2-nitrophenyl)piperidine-4-carboxamide; N-(7-Hydroxy-5,6,7,8-tetrahydronaphthalen-1-yl)-1-[2-nitro-4-(trifluoromethyl)phenyl]piperidine-4-carboxamide; 1-(2-Fluorophenyl)-N-(7-hydroxy-5,6,7,8-tetrahydronaphthalen-1-yl)piperidine-4-carboxamide; 1-(4-Fluorophenyl)-N-(7-hydroxy-5,6,7,8-tetrahydronaphthalen-1-yl)piperidine-4-carboxamide; 1-[4-Chloro-2-(trifluoromethyl)phenyl]-N-(7-hydroxy-5,6,7,8-tetrahydronaphthalen-1-yl)piperidine-4-carboxamide; N-(7-Hydroxy-5,6,7,8-tetrahydronaphthalen-1-yl)-1-[4-(trifluoromethyl)phenyl]piperidine-4-carboxamide; 1-[2-Chloro-4-(trifluoromethyl)phenyl]-N-(7-hydroxy-5,6,7,8-tetrahydronaphthalen-1-yl)piperidine-4-carboxamide; 1-(4-Fluorophenyl)-N-[(7R)-7-hydroxy-5,6,7,8-tetrahydronaphthalen-1-yl]piperidine-4-carboxamide; 1-[2-Chloro-4-(trifluoromethyl)phenyl]-N-[(7R)-7-hydroxy-5,6,7,8-tetrahydronaphthalen-1-yl]piperidine-4-carboxamide; 1-[2-Chloro-4-(trifluoromethyl)phenyl]-N-[(7S)-7-hydroxy-5,6,7,8-tetrahydro-naphthalen-1-yl]piperidine-4-carboxamide; 1-[3-Chlorophenyl]-N-[(7R)-7-hydroxy-5,6,7,8-tetrahydronaphthalen-1-yl]piperidine-4-carboxamide; N-[(7R)-7-Hydroxy-1-phenyl-5,6,7,8-tetrahydronaphthalen-1-yl]piperidine-4-carboxamide; N-[(7R)-7-Hydroxy-5,6,7,8-tetrahydronaphthalen-1-yl]-1-[3-trifluoromethyl-phenyl]piperidine-4-carboxamide; N-[(7R)-7-Hydroxy-5,6,7,8-tetrahydronaphthalen-1-yl]-1-[3-trifluoromethoxy-phenyl]piperidine-4-carboxamide; 1-[2,4-Dichlorophenyl]-N-[(7R)-7-hydroxy-5,6,7,8-tetrahydronaphthalen-1-yl]piperidine-4-carboxamide; 1-[3,4-Bis[trifluoromethoxy]phenyl]-N-[(7R)-7-hydroxy-5,6,7,8-tetrahydro-naphthalen-1-yl]piperidine-4-carboxamide; N-[(7R)-7-Hydroxy-5,6,7,8-tetrahydronaphthalen-1-yl]-1-[4-trifluoromethoxy-phenyl]piperidine-4-carboxamide; N-[(7R)-7-Hydroxy-5,6,7,8-tetrahydronaphthalen-1-yl]-1-[4-trifluoromethyl-pyrimidin-2-yl]piperidine-4-carboxamide; 1-[5-Chloropyrimidin-2-yl]-N-[(7R)-7-hydroxy-5,6,7,8-tetrahydronaphthalen-1-yl]piperidine-4-carboxamide; 1-[2-Chloro-4-nitrophenyl]-N-[(7R)-7-hydroxy-5,6,7,8-tetrahydronaphthalen-1-yl]piperidine-4-carboxamide; 1-[3-(Acetylamino)-5-(trifluoromethyl)pyridin-2-yl]-N-[(7R)-7-hydroxy-5,6,7,8-tetrahydronaphthalen-1-yl]piperidine-4-carboxamide; N-[(7R)-7-Hydroxy-5,6,7,8-tetrahydronaphthalen-1-yl]-1-[5-(trifluoromethyl)-pyridin-2-yl]piperidine-4-carboxamide; N-[(7R)-7-Hydroxy-5,6,7,8-tetrahydronaphthalen-1-yl]-1-[4-trifluoromethyl-phenyl]piperidine-4-carboxamide; and salts thereof.

\* \* \* \* \*

UNITED STATES PATENT AND TRADEMARK OFFICE
CERTIFICATE OF CORRECTION

PATENT NO. : 7,615,557 B2
APPLICATION NO. : 10/574122
DATED : November 10, 2009
INVENTOR(S) : Bouchon et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 336 days.

Signed and Sealed this

Nineteenth Day of October, 2010

David J. Kappos
*Director of the United States Patent and Trademark Office*